United States Patent [19]

Ueno et al.

[11] Patent Number: 5,391,776

[45] Date of Patent: Feb. 21, 1995

[54] STEROID DERIVATIVES

[75] Inventors: Hiroaki Ueno, San Diego, Calif.; Syuichiro Kadowaki, Kanagawa, Japan; Akihito Kamizono, Tokyo, Japan; Masahiko Morioka, Tokyo, Japan; Akihisa Mori, Tokyo, Japan

[73] Assignee: Mitsubishi Kasei Corporation, Tokyo, Japan

[21] Appl. No.: 15,800

[22] Filed: Feb. 10, 1993

[30] Foreign Application Priority Data

Feb. 14, 1992 [JP] Japan .................................. 4-028497

[51] Int. Cl.⁶ ............................................. C07J 51/00
[52] U.S. Cl. ..................................... 552/507; 552/506
[58] Field of Search ................ 552/507, 506; 514/102, 514/107

[56] References Cited

FOREIGN PATENT DOCUMENTS

| | | |
|---|---|---|
| 0496520 | 7/1992 | European Pat. Off. . |
| 0548884 | 6/1993 | European Pat. Off. . |
| 2-104593 | 4/1990 | Japan . |
| WO92/05187 | 4/1992 | WIPO . |

OTHER PUBLICATIONS

Eriksen et al., Science, vol. 241, pp. 84–86 Jul. 1988.

*Primary Examiner*—Paul J. Killos
*Attorney, Agent, or Firm*—Wenderoth, Lind & Ponack

[57] ABSTRACT

Asteroid derivative of the general formula:

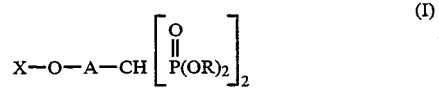

wherein X—O— represents a residue of steroid compound and —A— represents —CO[NH(CHR$^1$)$_y$—(Y)$_p$—CO]$_m$NH—, —CO—(R$^2$)$_x$—(Z)$_q$—CO—NH—, or —CO—(CH$_2$)$_n$—. A therapeutic agent to osteopathy comprising the above steroid derivative is also provided.

10 Claims, No Drawings

STEROID DERIVATIVES

The present invention relates to novel steroid derivatives. More particularly, this invention relates to steroid derivatives useful as therapeutic agents in osteopathy such as osteoporosis or the like and pharmaceutical compositions containing at least one of them.

Steroids (e.g. estrogen, androgen) already known as having sexual hormone activity have been noted to be useful as therapeutic agents in the treatment of osteoporosis, because they show osteogenesis accelerating activity and increase the bone volume [New England Journal of Medicine, 303, 1195 (1980); Journal of Clinical and Endocrinological Metabolism, 51, 1359 (1980)]. Further, it has recently been recognized that these steroid compounds accelerate osteogenesis by direct action to bone, because receptors for estrogen or androgen were found in bone tissue [Science, 241, 84 (1988); Proceedings of the National Academy of Sciences of the U.S.A., .86, 854 (1989)]. However, these steroid compounds require careful administration when used as a systemic therapeutic agent for osteoporosis, because they also act on sexual organs and induce several side effects, such as generation of uterus cancer, abnormal uterine bleeding, prostatic hypertrophy, defemination or the like.

On the other hand, bisphosphonic acid derivatives are known easily to transfer to bone, and it is disclosed that a medicinal compound can be osteoselectively taken in by binding said medicinal compound to a bisphosphonic acid derivative [Japanese Patent Publications (KOKAI) No. SHO 58-174393, SHO 62-26256 and HEI 2-104593]. These publications disclose as a medicinal compound carbonic acid dehydrogenase inhibitors, antiinflammatory agents, anticancer agents and the like. However, a compound consisting of a steroid compound bound to a bisphosphonic acid derivative is not disclosed in the publications.

As the results of extensive studies seeking an effective means which allows a steroid compound to osteoselectively act, the present inventors have found that administration of a novel compound prepared by binding a steroid compound to a bisphosphonic acid derivative through one of various spacers enables the steroid compound to act more selectively on osseous tissue than other organs. A conjugate of a steroid compound and a bisphosphonic acid derivative exerts no steroid-like activity, since it does not bind to a steroid receptor. It is considered, however, that when said conjugate is administered to a living body, a considerable part of said conjugate molecules would be adsorbed on bones through the bisphosphonic acid, and the rest remained without being adsorbed would be smoothly excreted out of the body. The conjugate bound to the bone is gradually cleaved at the bonding site of the bisphosphonic acid and steroid compound to isolate the steroid compound which will bind to the steroid receptor within the bone, thereby osseoselectively showing osseogenesis accelerating activity. Further, the present inventors have found that the concentration of the steroid compound in bone can be kept at a high level for a long time. The present invention has been established based on the above findings.

Accordingly, the present invention is directed to a steroid derivative of the general formula (I):

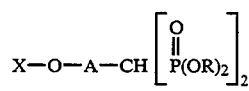

wherein X—O— represents a residue of steroid compound, —A— represents

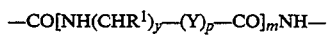

in which y represents an integer of from 1 to 3, p represents 0 or 1, m represents an integer of from 0 to 5, $R^1$ represents hydrogen atom, optionally substituted $C_1$-$C_4$ alkyl group or optionally substituted $C_6$-$C_{14}$ aryl group, and Y represents —O— or —NH—,

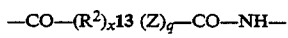

which x and q each independently represent 0 or 1, $R^2$ represents optionally substituted vinylene group,

in which k and l each represent an integer of 0–5, and Cyclo represents $C_3$-$C_7$ cycloalkylene, optionally substituted phenylene group or optionally substituted $C_1$-$C_7$ alkylene group, Z represents —O— or —NH—, or

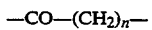

in which n represents an integer of from 0 to 10 with the proviso that, when X—O— is 17β-(3-hydroxy-1,3,5-estratrienenyloxy) group, n represents 0 or 1, and R represents hydrogen atom or $C_1$-$C_4$ alkyl group, or pharmaceutically acceptable salts thereof. The present invention will be explained in detail below.

The present invention relates to steroid derivatives of the general formula (I):

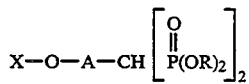

wherein X—O— represents a residue of steroid compounds having a cyclopentanohydrophenanthrene ring, so-called "steroid nucleus", which is represented by the following formula:

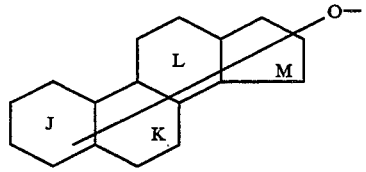

wherein the rings J, K, L, and M each independently represent a saturated, partially saturated, or unsaturated ring, and they may be independently substituted by one or more substituents selected from alkyl, alkenyl, alkynyl, halogen, alkoxy, ester, acyl, hydroxy, and oxo groups. Specific examples are, for instance, those having hydroxy group (e.g. estradiol, testosterone, dehydrotestosterone, pregnenolone, ethynylestradiol, estrone, estriol, dehydroepiandrosterone, androstenediol, 17α-hydroxyprogesterone, norethandrolone, androsterone, norethidrone, nandrolone, etc.), and —A— represents —CO[NH(CHR$^1$)$_y$—(Y)$_p$—CO]$_m$NH— in which y represents an integer from 1 to 3, p represents 0 or 1, m represents an integer from 0 to 5, R$^1$ represents hydrogen atom, C$_1$-C$_4$ alkyl group optionally having a substituent (e.g. hydroxy group, mercapto group, alkylthio group, amino group, amido group, carboxy group, optionally substituted phenyl group, etc.) or C$_6$-C$_{14}$ aryl group optionally having one or more substituents selected from hydroxy group, carboxy group and C$_1$-C$_5$ alkyl group, and Y represents —O— or NH—, or —CO—(R$^2$)$_x$—(Z)$_q$—CO—NH— in which x and q each independently represent 0 or 1, R$^2$ represents vinylene group optionally substituted by a substituent (e.g. hydroxy group, C$_1$-C$_5$ alkyl group, C$_7$-C$_{20}$ aralkyl group, carboxy group, etc.), —(CH$_2$)$_k$—Cyclo—(CH$_2$)$_l$— in which k and l each represent an integer of 0-5, and Cyclo represents C$_3$-C$_7$ cycloalkylene group which includes divalent groups formed by elimination of two hydrogen atoms from a single carbon atom to which they attached (e.g. cyclopropylene group, cyclopentalene group, cycloheptalene group, etc.)), phenyl group optionally substituted by a substituent (e.g. hydroxy group, carboxy group, C$_1$-C$_5$ alkyl group, etc.) or C$_1$-C$_7$ alkylene group (e.g. methylene, methylene, propylene, pentamethylene, heptamethylene, etc.) optionally substituted by a substituent (e.g. hydroxy group, C$_1$-C$_5$ alkyl group, C$_7$-C$_{20}$ aralkyl group, carboxy group, etc.), and Z represents —O— or —NH—, or —CO—(CH$_2$)$_n$— in which n represents an integer from 0 to 10 with the proviso that, when X—O— is 17η-(3-hydroxy-1,3,5-estratrienenyloxy) group, n represents 0 or 1, and R represents hydrogen atom or C$_1$-C$_4$ alkyl group (e.g. methyl group, butyl group, etc.), or pharmaceutically acceptable salts thereof.

Specific examples of the compounds of the present invention will be shown below in Table 1.

TABLE 1

$$X-O-A-CH[\overset{\overset{O}{\|}}{P}(OR)_2]_2$$

| Compd. No. | X—O— | —A— | R |
|---|---|---|---|
| 1 | 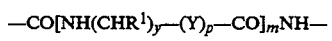 | —C(=O)—NHCH$_2$—C(=O)—N— | H |
| 2 | 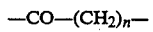 | —C(=O)—NH(CH$_2$)$_2$C(=O)—NH— | H |
| 3 | 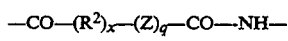 | —C(=O)—NH(CH$_2$)$_3$C(=O)—NH— | H |
| 4 |  | —C(=O)—NHCH(CH$_3$)C(=O)—NH— | H |

TABLE 1-continued $$X-O-A-CH[P(OR)_2]_2 \quad (\text{with } =O \text{ on P})$$

| Compd. No. | X—O— | —A— | R |
|---|---|---|---|
| 5 | estradiol-17-O— | —C(O)—NHCHC(O)—NH— with CH(CH₃)₂ | H |
| 6 | estradiol-17-O— | —C(O)—NHCHC(O)—NH— with CH₂CH(CH₃)₂ | H |
| 7 | estradiol-17-O— | —C(O)—NHCHC(O)—NH— with CH(CH₃)(C₂H₅) | H |
| 8 | estradiol-17-O— | —C(O)—NHCHC(O)—NH— with CH₂–C₆H₅ | H |
| 9 | estradiol-17-O— | —C(O)—NHCHC(O)—NH— with CH₂–C₆H₄–OH | H |
| 10 | estradiol-17-O— | —C(O)—NHCHC(O)—NH— with CH₂OH | H |

TABLE 1-continued $$X-O-A-CH[P(OR)_2]_2$$ (with =O on P)

| Compd. No. | X—O— | —A— | R |
|---|---|---|---|
| 11 | estradiol 17-O— | —C(=O)—NHCHC(=O)—NH— with side chain CH(OH)(CH₃) | H |
| 12 | estradiol 17-O— | —C(=O)—NHCHC(=O)—NH— with side chain CH₂SH | H |
| 13 | estradiol 17-O— | —C(=O)—NHCHC(=O)—NH— with side chain CH₂CH₂SCH₃ | H |
| 14 | estradiol 17-O— | —C(=O)—NHCHC(=O)—NH— with side chain (CH₂)₄—NH₂ | H |
| 15 | estradiol 17-O— | —C(=O)—NHCHC(=O)—NH— with side chain CH₂COOH | H |
| 16 | estradiol 17-O— | —C(=O)—NHCHC(=O)—NH— with side chain CH₂CONH₂ | H |

TABLE 1-continued $$X-O-A-CH[\overset{O}{\underset{\|}{P}}(OR)_2]_2$$

| Compd. No. | X—O— | —A— | R |
|---|---|---|---|
| 17 | estradiol-17-O— (3-HO) | $-\overset{O}{\underset{\|}{C}}-NH-\underset{\underset{CH_2CH_2COOH}{\|}}{CH}-\overset{O}{\underset{\|}{C}}-NH-$ | H |
| 18 | estradiol-17-O— (3-HO) | $-\overset{O}{\underset{\|}{C}}-NH-\underset{\underset{CH_2CH_2CONH_2}{\|}}{CH}-\overset{O}{\underset{\|}{C}}-NH-$ | H |
| 19 | estradiol-17-O— (3-HO) | $-\overset{O}{\underset{\|}{C}}-NH-$ | H |
| 20 | estradiol-17-O— (3-HO) | $-\overset{O}{\underset{\|}{C}}(-NHCH_2-)_2\overset{O}{\underset{\|}{C}}-NH-$ | H |
| 21 | estradiol-17-O— (3-HO) | $-\overset{O}{\underset{\|}{C}}(-NHCH_2-)_3\overset{O}{\underset{\|}{C}}-NH-$ | H |
| 22 | estradiol-17-O— (3-HO) | $-\overset{O}{\underset{\|}{C}}(-NHCH_2-)_4\overset{O}{\underset{\|}{C}}-NH-$ | H |

TABLE 1-continued $$X-O-A-CH[P(O)(OR)_2]_2$$

| Compd. No. | X—O— | —A— | R |
|---|---|---|---|
| 23 | estradiol-17-O— (3-OH) | —C(O)+NHCH$_2$C(O)$\overline{)_5}$NH— | H |
| 24 | estradiol-17-O— (3-OH) | —C(O)—C(O)—NH— | H |
| 25 | estradiol-17-O— (3-OH) | —C(O)—CH$_2$—C(O)—NH— | H |
| 26 | estradiol-17-O— (3-OH) | —C(O)—(CH$_2$)$_2$—C(O)—NH— | H |
| 27 | estradiol-17-O— (3-OH) | —C(O)—(CH$_2$)$_3$—C(O)—NH— | H |
| 28 | estradiol-17-O— (3-OH) | —C(O)—(CH$_2$)$_4$—C(O)—NH— | H |

TABLE 1-continued $$X-O-A-CH[\overset{\overset{O}{\|}}{P}(OR)_2]_2$$

| Compd. No. | X—O— | —A— | R |
|---|---|---|---|
| 29 | [estradiol 17-methoxy, 3-OH] | $-\overset{\overset{O}{\|}}{C}-(CH_2)_5-\overset{\overset{O}{\|}}{C}-NH-$ | H |
| 30 | [estradiol 17-methoxy, 3-OH] | $-\overset{\overset{O}{\|}}{C}-\underset{\underset{CH_3}{\|}}{CH}-\overset{\overset{O}{\|}}{C}-NH-$ | H |
| 31 | [estradiol 17-O, 3-H] | $-\overset{\overset{O}{\|}}{C}-\underset{\underset{C_2H_5}{\|}}{CH}-\overset{\overset{O}{\|}}{C}-NH-$ | H |
| 32 | [estradiol 17-O, 3-H] | $-\overset{\overset{O}{\|}}{C}-\underset{\underset{CH_3}{\|}}{\overset{\overset{CH_3}{\|}}{C}}-\overset{\overset{O}{\|}}{C}-NH-$ | H |
| 33 | [estradiol 17-O, 3-H] | $-\overset{\overset{O}{\|}}{C}-\underset{\underset{C_2H_5}{\|}}{\overset{\overset{C_2H_5}{\|}}{C}}-\overset{\overset{O}{\|}}{C}-NH-$ | H |
| 34 | [estradiol 17-O, 3-H] | $-\overset{\overset{O}{\|}}{C}-\text{(cyclopentyl)}-\overset{\overset{O}{\|}}{C}-NH-$ | H |
| 35 | [estradiol 17-O, 3-H] | $-\overset{\overset{O}{\|}}{C}-\text{(cyclohexyl)}-\overset{\overset{O}{\|}}{C}-NH-$ | H |

TABLE 1-continued
$$X-O-A-CH[P(OR)_2]_2$$
$$\phantom{X-O-A-CH[}\overset{\overset{O}{\parallel}}{\phantom{P}}\phantom{(OR)_2]_2}$$
| Compd. No. | X—O— | —A— | R |
|---|---|---|---|
| 36 | 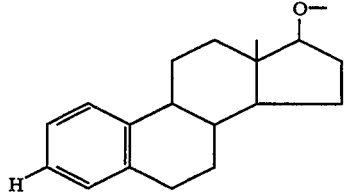 | 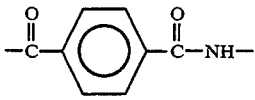 | H |
| 37 | 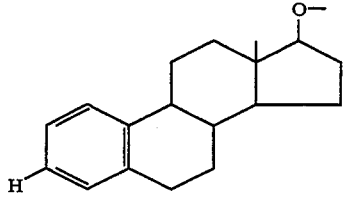 | 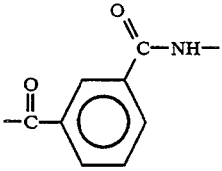 | H |
| 38 | 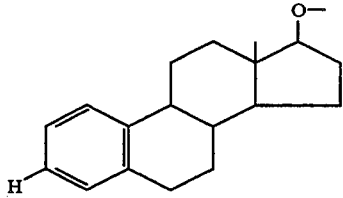 | 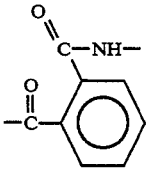 | H |
| 39 | 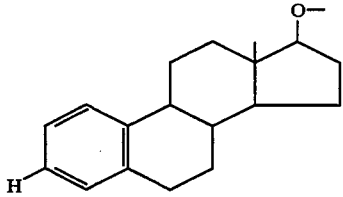 | 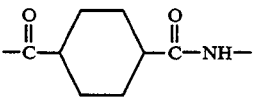 | H |
| 40 | 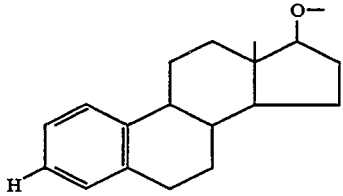 | 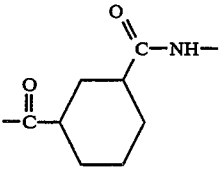 | H |
| 41 | 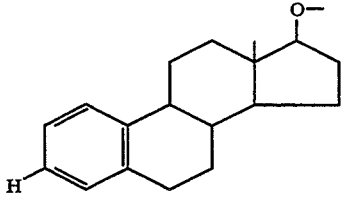 | 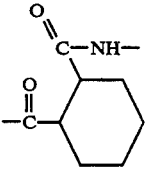 | H |
| 42 | 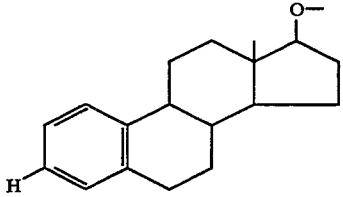 | 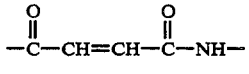 | H |

TABLE 1-continued $$X-O-A-CH[\overset{O}{\underset{\|}{P}}(OR)_2]_2$$

| Compd. No. | X—O— | —A— | R |
|---|---|---|---|
| 43 | [estradiol-17-O—] | $-\overset{O}{\underset{\|}{C}}NH-(CH_2)_2NH\overset{O}{\underset{\|}{C}}NH-$ | H |
| 44 | [estradiol-17-O—] | $-\overset{O}{\underset{\|}{C}}NH-(CH_2)_2-O-\overset{O}{\underset{\|}{C}}-NH-$ | H |
| 45 | [estradiol-17-O—] | $-\overset{O}{\underset{\|}{C}}-CH_2NH\overset{O}{\underset{\|}{C}}-NH-$ | H |
| 46 | [estradiol-17-O—] | $-\overset{O}{\underset{\|}{C}}-(CH_2)_2NH\overset{O}{\underset{\|}{C}}-NH-$ | H |
| 47 | [estradiol-17-O—] | $-\overset{O}{\underset{\|}{C}}-(CH_2)_3-NH-\overset{O}{\underset{\|}{C}}-NH-$ | H |
| 48 | [estradiol-17-O—] | $-\overset{O}{\underset{\|}{C}}-\underset{CH_3}{\underset{\|}{CH}}-NH\overset{O}{\underset{\|}{C}}NH-$ | H |
| 49 | [estradiol-17-O—] | $-\overset{O}{\underset{\|}{C}}-\text{C}_6\text{H}_4-N\overset{H}{\underset{\|}{\overset{O}{\|}{C}}}-NH-$ | H |

TABLE 1-continued $$X-O-A-\overset{O}{\underset{\|}{C}H[P(OR)_2]_2}$$

| Compd. No. | X—O— | —A— | R |
|---|---|---|---|
| 50 | estradiol-17-O— | —C(=O)—C₆H₁₀—NH—C(=O)—NH— | H |
| 51 | estradiol-17-O— | —C(=O)—CH₂—O—C(=O)—NH— | H |
| 52 | estradiol-17-O— | —C(=O)—(CH₂)₂—O—C(=O)—NH— | H |
| 53 | estradiol-17-O— | —C(=O)—C₆H₄—O—C(=O)—NH— | H |
| 54 | estradiol-17-O— | —C(=O)—C₆H₁₀—O—C(=O)—NH— | H |
| 55 | estradiol-17-O— | —C(=O)— | H |
| 56 | estradiol-17-O— | —C(=O)—CH₂— | H |

TABLE 1-continued $$X-O-A-CH[\overset{O}{\overset{\|}{P}}(OR)_2]_2$$

| Compd. No. | X—O— | —A— | R |
|---|---|---|---|
| 57 | 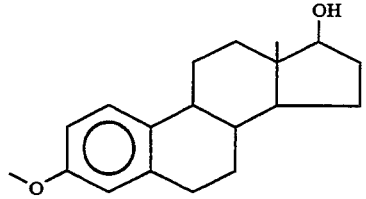 | $-\overset{O}{\overset{\|}{C}}NHCH_2\overset{O}{\overset{\|}{C}}-NH-$ | H |
| 58 |  | $-\overset{O}{\overset{\|}{C}}NH(CH_2)_2\overset{O}{\overset{\|}{C}}-NH-$ | H |
| 59 | 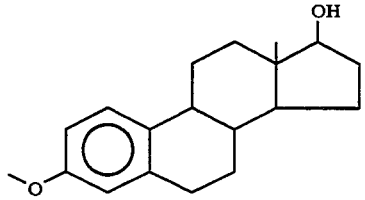 | $-\overset{O}{\overset{\|}{C}}NH(CH_2)_3\overset{O}{\overset{\|}{C}}NH-$ | H |
| 60 | 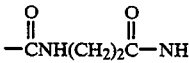 | $-\overset{O}{\overset{\|}{C}}-NH\underset{CH_3}{CH}\overset{O}{\overset{\|}{C}}NH-$ | H |
| 61 | 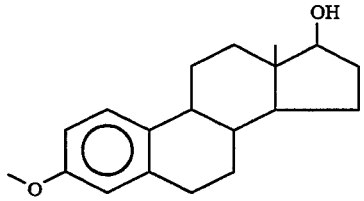 | $-\overset{O}{\overset{\|}{C}}NH\underset{CH(CH_3)_2}{CH}\overset{O}{\overset{\|}{C}}NH-$ | H |
| 62 | 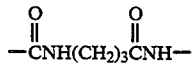 | $-\overset{O}{\overset{\|}{C}}-NH\underset{CH_2-C_6H_5}{CH}\overset{O}{\overset{\|}{C}}-NH-$ | H |
| 63 | 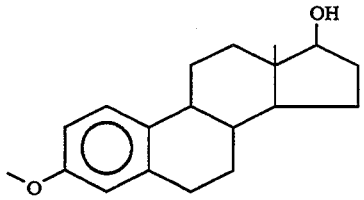 | $-\overset{O}{\overset{\|}{C}}NH-$ | H |

TABLE 1-continued $$X-O-A-CH[\overset{O}{\underset{}{P}}(OR)_2]_2$$

| Compd. No. | X—O— | —A— | R |
|---|---|---|---|
| 64 | [3-methoxy estradiol structure] | —C(NHCH₂C)₂NH— with two C=O groups | H |
| 65 | [3-methoxy estradiol structure] | —C(=O)—C(=O)—NH— | H |
| 66 | [3-methoxy estradiol structure] | —C(=O)—CH₂—C(=O)—NH— | H |
| 67 | [3-methoxy estradiol structure] | —C(=O)—(CH₂)₂—C(=O)—NH— | H |
| 68 | [3-methoxy estradiol structure] | —C(=O)—(CH₂)₃—C(=O)—NH— | H |
| 69 | [3-methoxy estradiol structure] | —C(=O)—CH(CH₃)—C(=O)—NH— | H |
| 70 | [3-methoxy estradiol structure] | —C(=O)—CH(C₂H₅)—C(=O)—NH— | H |

TABLE 1-continued
$$X-O-A-CH[P(OR)_2]_2$$
$$\phantom{X-O-A-CH[}\overset{O}{\|}\phantom{)_2]_2}$$
| Compd. No. | X—O— | —A— | R |
|---|---|---|---|
| 71 | 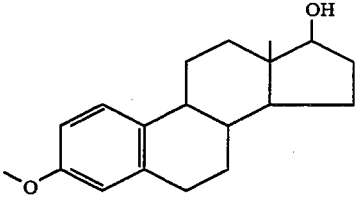 | 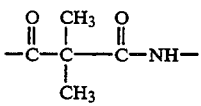 | H |
| 72 | 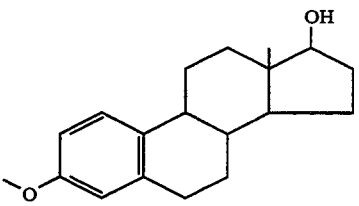 | 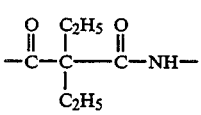 | H |
| 73 | 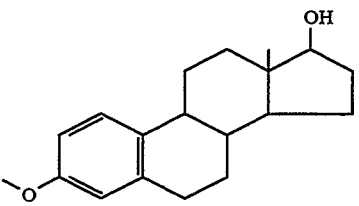 |  | H |
| 74 | 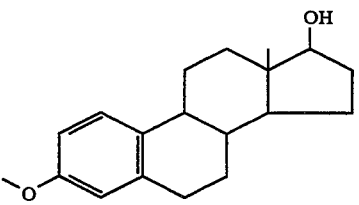 | 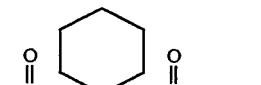 | H |
| 75 | 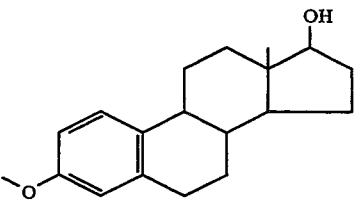 | 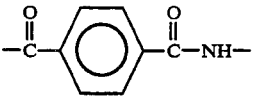 | H |
| 76 | 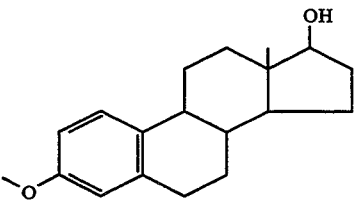 | 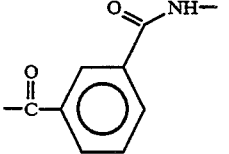 | H |
| 77 | 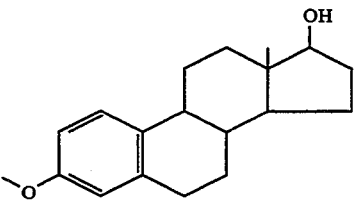 | 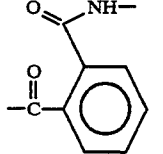 | H |

TABLE 1-continued
$$X-O-A-CH[\overset{\overset{O}{\|}}{P}(OR)_2]_2$$
| Compd. No. | X—O— | —A— | R |
|---|---|---|---|
| 78 | 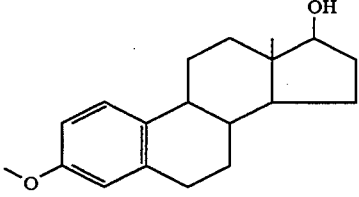 | 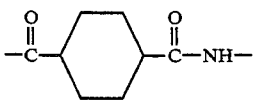 | H |
| 79 | 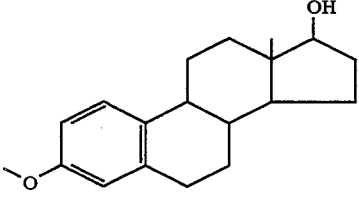 | 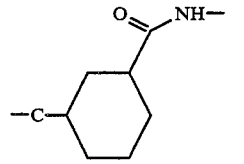 | H |
| 80 | 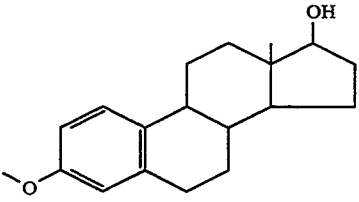 | 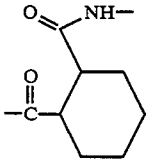 | H |
| 81 | 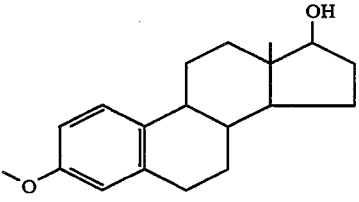 | 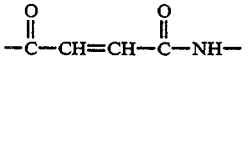 | H |
| 82 | 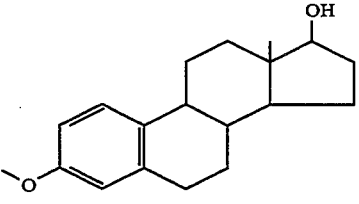 | $-\overset{\overset{O}{\|}}{C}-NH(CH_2)_2NH\overset{\overset{O}{\|}}{C}NH-$ | H |
| 83 | 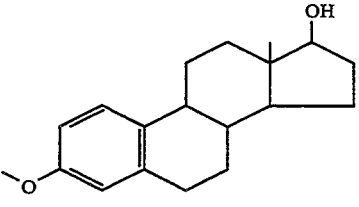 | $-\overset{\overset{O}{\|}}{C}-NH(CH_2)_2-O-\overset{\overset{O}{\|}}{C}NH-$ | H |
| 84 | 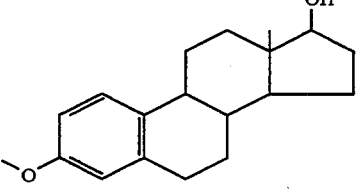 | $-\overset{\overset{O}{\|}}{C}CH_2NH\overset{\overset{O}{\|}}{C}-NH-$ | H |

TABLE 1-continued $$X-O-A-CH[\overset{\overset{O}{\|}}{P}(OR)_2]_2$$

| Compd. No. | X—O— | —A— | R |
|---|---|---|---|
| 85 | 3-methoxy-estradiol | $-\overset{O}{\overset{\|}{C}}(CH_2)_2NH\overset{O}{\overset{\|}{C}}NH-$ | H |
| 86 | 3-methoxy-estradiol | $-\overset{O}{\overset{\|}{C}}\text{-}C_6H_4\text{-}N(H)\overset{O}{\overset{\|}{C}}NH-$ | H |
| 87 | 3-methoxy-estradiol | $-\overset{O}{\overset{\|}{C}}\text{-}C_6H_{10}\text{-}N(H)\overset{O}{\overset{\|}{C}}NH-$ | H |
| 88 | 3-methoxy-estradiol | $-\overset{O}{\overset{\|}{C}}\text{-}CH_2\text{-}O\text{-}\overset{O}{\overset{\|}{C}}NH-$ | H |
| 89 | 3-methoxy-estradiol | $-\overset{O}{\overset{\|}{C}}\text{-}(CH_2)_2O\text{-}\overset{O}{\overset{\|}{C}}NH-$ | H |
| 90 | 3-methoxy-estradiol | $-\overset{O}{\overset{\|}{C}}\text{-}C_6H_4\text{-}O\text{-}\overset{O}{\overset{\|}{C}}NH-$ | H |
| 91 | 3-methoxy-estradiol | $-\overset{O}{\overset{\|}{C}}\text{-}C_6H_{10}\text{-}O\text{-}\overset{O}{\overset{\|}{C}}NH-$ | H |

TABLE 1-continued
$$X-O-A-CH[P(OR)_2]_2 \overset{O}{\|}$$
| Compd. No. | X—O— | —A— | R |
|---|---|---|---|
| 92 | 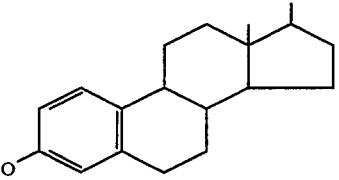 | $-\overset{O}{\underset{\|}{C}}-$ | H |
| 93 | 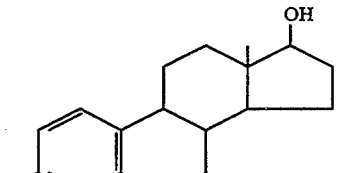 | $-\overset{O}{\underset{\|}{C}}-CH_2-$ | H |
| 94 | 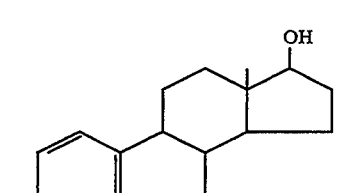 | $-\overset{O}{\underset{\|}{C}}-(CH_2)_2-$ | H |
| 95 | 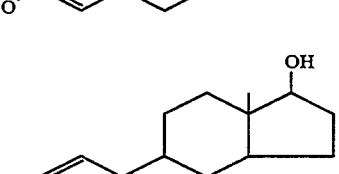 | $-\overset{O}{\underset{\|}{C}}-(CH_2)_3-$ | H |
| 96 | 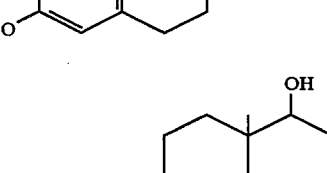 | $-\overset{O}{\underset{\|}{C}}-(CH_2)_4-$ | H |
| 97 | 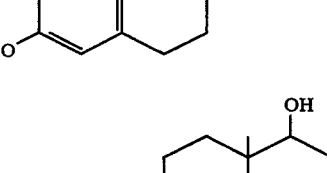 | $-\overset{O}{\underset{\|}{C}}-(CH_2)_6-$ | H |
| 98 | 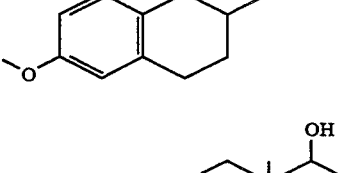 | $-\overset{O}{\underset{\|}{C}}-(CH_2)_{10}-$ | H |

TABLE 1-continued $$X-O-A-CH[P(O)(OR)_2]_2$$

| Compd. No. | X—O— | —A— | R |
|---|---|---|---|
| 99 | 3-methoxy-estra-1,3,5(10)-trien-17-one (3-O-) | —C(O)NHCH$_2$C(O)NH— | H |
| 100 | 3-methoxy-estra-1,3,5(10)-trien-17-one (3-O-) | —C(O)—CH$_2$—C(O)—NH— | H |
| 101 | 3-methoxy-estra-1,3,5(10)-trien-17-one (3-O-) | —C(O)—(CH$_2$)$_2$—C(O)—NH— | H |
| 102 | 3-methoxy-estra-1,3,5(10)-trien-17-one (3-O-) | —C(O)—CH$_2$— | H |
| 103 | 17-hydroxy-androst-4-en-3-one (17-O-, 17-methyl) | —C(O)—NHCH$_2$C(O)—NH— | H |
| 104 | 17-hydroxy-androst-4-en-3-one (17-O-, 17-methyl) | —C(O)—CH$_2$—C(O)—NH— | H |
| 105 | 17-hydroxy-androst-4-en-3-one (17-O-, 17-methyl) | —C(O)—(CH$_2$)$_2$—C(O)—NH— | H |

TABLE 1-continued $$X-O-A-CH[P(O)(OR)_2]_2$$

| Compd. No. | X—O— | —A— | R |
|---|---|---|---|
| 106 | [17β-methoxy-androst-4-en-3-one steroid] | $-\overset{O}{\underset{\|}{C}}-CH_2-$ | H |
| 107 | [17β-methoxy-5α-androstan-3-one steroid] | $-\overset{O}{\underset{\|}{C}}-NHCH_2\overset{O}{\underset{\|}{C}}-NH-$ | H |
| 108 | [17β-methoxy-5α-androstan-3-one steroid] | $-\overset{O}{\underset{\|}{C}}-CH_2\overset{O}{\underset{\|}{C}}-NH-$ | H |
| 109 | [17β-methoxy-5α-androstan-3-one steroid] | $-\overset{O}{\underset{\|}{C}}-(CH_2)_2\overset{O}{\underset{\|}{C}}-NH-$ | H |
| 110 | [17β-methoxy-5α-androstan-3-one steroid] | $-\overset{O}{\underset{\|}{C}}-CH_2-$ | H |
| 111 | [3β-methoxy-androst-5-en-17-one steroid] | $-\overset{O}{\underset{\|}{C}}-NHCH_2\overset{O}{\underset{\|}{C}}-NH-$ | H |
| 112 | [3β-methoxy-androst-5-en-17-one steroid] | $-\overset{O}{\underset{\|}{C}}-CH_2\overset{O}{\underset{\|}{C}}-NH-$ | H |

TABLE 1-continued $$X-O-A-CH[P(OR)_2]_2$$
$$\phantom{X-O-A-CH[}\|\phantom{P(OR)_2]_2}$$
$$\phantom{X-O-A-CH[P}O\phantom{R)_2]_2}$$

| Compd. No. | X—O— | —A— | R |
|---|---|---|---|
| 113 | 3-methoxy-androst-5-en-17-one (3-O-) | —C(O)—(CH$_2$)$_2$—C(O)NH— | H |
| 114 | 3-methoxy-androst-5-en-17-one (3-O-) | —C(O)—CH$_2$— | H |
| 115 | 3-methoxy-androst-5-en-17-ol (3-O-) | —C(O)—NHCH$_2$C(O)—NH— | H |
| 116 | 3-methoxy-androst-5-en-17-ol (3-O-) | —C(O)—CH$_2$—C(O)—NH— | H |
| 117 | 3-methoxy-androst-5-en-17-ol (3-O-) | —C(O)—(CH$_2$)$_2$—C(O)NH— | H |
| 118 | 3-methoxy-androst-5-en-17-ol (3-O-) | —C(O)—CH$_2$— | H |
| 119 | 17-methoxy-androst-5-en-3-ol (3-O-) | —C(O)—NHCH$_2$C(O)—NH— | H |

TABLE 1-continued $$X-O-A-CH[P(OR)_2]_2\overset{O}{\|}$$

| Compd. No. | X—O— | —A— | R |
|---|---|---|---|
| 120 | [3β-hydroxy-androst-5-en-17β-yloxy] | —C(O)—CH₂—C(O)—NH— | H |
| 121 | [3β-hydroxy-androst-5-en-17β-yloxy] | —C(O)—(CH₂)₂—C(O)—NH— | H |
| 122 | [3β-hydroxy-androst-5-en-17β-yloxy] | —C(O)—CH₂— | H |
| 123 | [3β-methoxy-pregn-5-en-20-one-yl] | —C(O)—NHCH₂—C(O)—NH— | H |
| 124 | [3β-methoxy-pregn-5-en-20-one-yl] | —C(O)—CH₂—C(O)—NH— | H |
| 125 | [3β-methoxy-pregn-5-en-20-one-yl] | —C(O)—(CH₂)₂—C(O)—NH— | H |

TABLE 1-continued $$X-O-A-CH[\overset{\overset{O}{\|}}{P}(OR)_2]_2$$

| Compd. No. | X—O— | —A— | R |
|---|---|---|---|
| 126 | (3-methoxy-pregn-5-en-20-one steroid) | $-\overset{\overset{O}{\|}}{C}-CH_2-$ | H |
| 127 | (17-oxy-pregn-4-ene-3,20-dione steroid) | $-\overset{\overset{O}{\|}}{C}-NHCH_2\overset{\overset{O}{\|}}{C}-NH-$ | H |
| 128 | (17-oxy-pregn-4-ene-3,20-dione steroid) | $-\overset{\overset{O}{\|}}{C}-CH_2\overset{\overset{O}{\|}}{C}-NH-$ | H |
| 129 | (17-oxy-pregn-4-ene-3,20-dione steroid) | $-\overset{\overset{O}{\|}}{C}-(CH_2)_2\overset{\overset{O}{\|}}{C}-NH-$ | H |
| 130 | (17-oxy-pregn-4-ene-3,20-dione steroid) | $-\overset{\overset{O}{\|}}{C}-CH_2-$ | H |
| 131 | (17-oxy-17-ethynyl-estra-1,3,5(10)-trien-3-ol steroid) | $-\overset{\overset{O}{\|}}{C}-NHCH_2\overset{\overset{O}{\|}}{C}-NH-$ | H |

TABLE 1-continued $$X-O-A-CH[\overset{O}{\underset{\|}{P}}(OR)_2]_2$$

| Compd. No. | X—O— | —A— | R |
|---|---|---|---|
| 132 | 17α-ethynyl-17β-methoxy estradiol (3-O-) | —C(=O)—CH₂—C(=O)—NH— | H |
| 133 | 17α-ethynyl-17β-methoxy estradiol (3-O-) | —C(=O)—(CH₂)₂—C(=O)—NH— | H |
| 134 | 17α-ethynyl-17β-methoxy estradiol (3-O-) | —C(=O)—CH₂— | H |
| 135 | 17α-ethynyl-17β-hydroxy 3-methoxy estradiol (17-O-) | —C(=O)—NHCH₂—C(=O)—NH— | H |
| 136 | 17α-ethynyl-17β-hydroxy 3-methoxy estradiol (17-O-) | —C(=O)—CH₂—C(=O)—NH— | H |
| 137 | 17α-ethynyl-17β-hydroxy 3-methoxy estradiol (17-O-) | —C(=O)—(CH₂)₂—C(=O)—NH— | H |
| 138 | 17α-ethynyl-17β-hydroxy 3-methoxy estradiol (17-O-) | —C(=O)—CH₂— | H |

TABLE 1-continued $$X-O-A-\overset{\overset{O}{\|}}{C}H[P(OR)_2]_2$$

| Compd. No. | X—O— | —A— | R |
|---|---|---|---|
| 139 | [estradiol 17-O— structure with HO at C3] | —C(O)—NHCH₂C(O)—NH— | $CH_3$ |
| 140 | [estradiol 17-O— structure with HO at C3] | —C(O)—NHCH₂C(O)—NH— | $CH_2CH_3$ |
| 141 | [estradiol 17-O— structure with HO at C3] | —C(O)—NHCH₂C(O)—NH— | $(CH_2)_2CH_3$ |
| 142 | [estradiol 17-O— structure with HO at C3] | —C(O)—NHCH₂C(O)—NH— | $CH(CH_3)_2$ |
| 143 | [estradiol 17-O— structure with HO at C3] | —C(O)—NHCH₂C(O)—NH— | $(CH_2)_3CH_3$ |
| 144 | [estradiol 17-O— structure with HO at C3] | —C(O)—NHCH₂C(O)—NH— | $CH_2CH(CH_3)_2$ |

TABLE 1-continued $$X-O-A-CH[\overset{\overset{O}{\|}}{P}(OR)_2]_2$$

| Compd. No. | X—O— | —A— | R |
|---|---|---|---|
| 145 | [estradiol-17-O— with 3-OH] | $-\overset{\overset{O}{\|}}{C}-NHCH_2\overset{\overset{O}{\|}}{C}-NH-$ | $CH(CH_3)CH_2CH_3$ |
| 146 | [estradiol-17-O— with 3-OH] | $-\overset{\overset{O}{\|}}{C}-NHCH_2\overset{\overset{O}{\|}}{C}-NH-$ | $C(CH_3)_3$ |
| 147 | [17-O—COCH$_3$ steroid with 3-O—] | $-\overset{\overset{O}{\|}}{C}-CH_2-CH_2-\overset{\overset{O}{\|}}{C}-NH-$ | H |
| 148 | [17-O-cyclohexanecarbonyl steroid with 3-O—] | $-\overset{\overset{O}{\|}}{C}-CH_2-CH_2-\overset{\overset{O}{\|}}{C}-NH-$ | H |
| 149 | [17-O-benzoyl steroid with 3-O—] | $-\overset{\overset{O}{\|}}{C}-CH_2-CH_2-\overset{\overset{O}{\|}}{C}-NH-$ | H |

The compounds of the present invention can be formulated into pharmaceutical formulations suitable for particular administration route together with conventional carriers when used as a medicine. For example, they can be prepared into formulations such as tablets, capsules, granules, powders, solutions or the like for oral route. In preparing solid formulations for oral route, customary excipients, binders, lubricants, coloring agents, disintegrators and the like may be used. Examples of the excipient are lactose, starch, talc, magnesium stearate, crystalline cellulose, methyl cellulose, carboxymethyl cellulose, glycerin, sodium alginate, arabic gum, and the like. Examples of the binder are polyvinyl alcohol, polyvinyl ether, ethyl cellulose, arabic gum, shellac, saccharose, and the like, and examples of the lubricant are magnesium stearate, talc and the like. In addition, customary coloring agents and disintegrators already known may be used. Further, tablets may be coated in a conventional manner. Liquid formulations include aqueous or oily suspensions, solutions, syrups, elixirs and the like and these liquid formulations may be prepared in a conventional manner. In preparing injections, the compound of the present invention may be mixed with pH regulators, buffers, stabilizers, isotonic agents, topical anesthetics, and the like, and injections for subcutaneous, intramuscular or intravenous administration may be prepared. As for the base for preparing suppositories, fatty and oily bases such as cacao butter, polyethylene glycol, Witepsol (Registered trademark, Dynamite Novel Company) or the like may be used.

Appropriate dosage of thus prepared formulations varies, depending upon the symptoms, body weight, age or the like of particular patients. Appropriate daily dosage for adult of the compound of the present invention is, in general, about 0.01 to 2000 mg. The daily dosage may preferably be administered after divided to 2–4 portions. Alternatively, a single dosage may be administered every other day or with longer time interval.

Salts of the steroid derivatives of the general formula (I) are those with non-toxic bases. Appropriate salts include those of inorganic bases such as sodium, potassium or the like, ammonium salt, those of organic bases like triethylamine, and the like.

Production of the compounds of the present invention will be explained below under three sections, depending upon the type of —A— in the general formula (I). (1) Compounds (III-g), (III-j), (III-n) of the general formula (I), in which —A— is

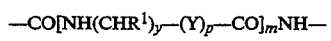

wherein $R^1$, y, Y, p and m have the same meanings as defined in the general formula (I), or their salts, can be prepared, for example, according to the following synthetic route.

i) Where p is 0:

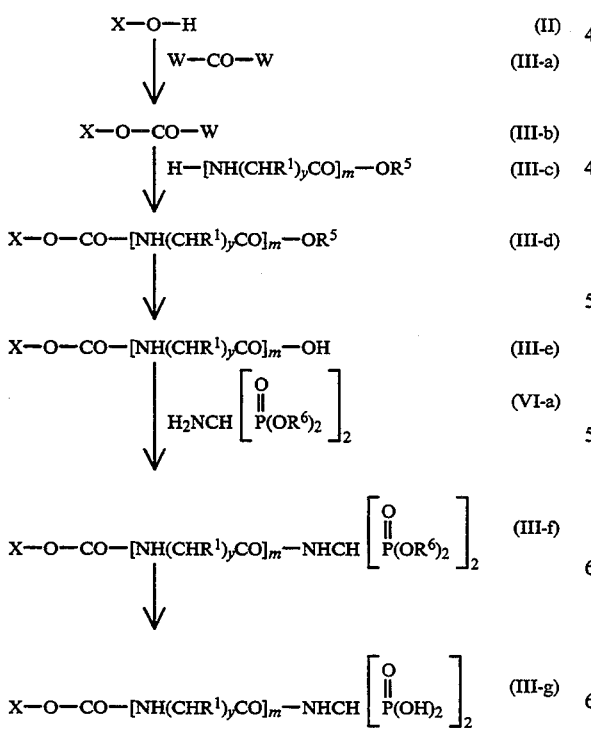

ii) Where p is 1 and Y is —NH— (m=1):

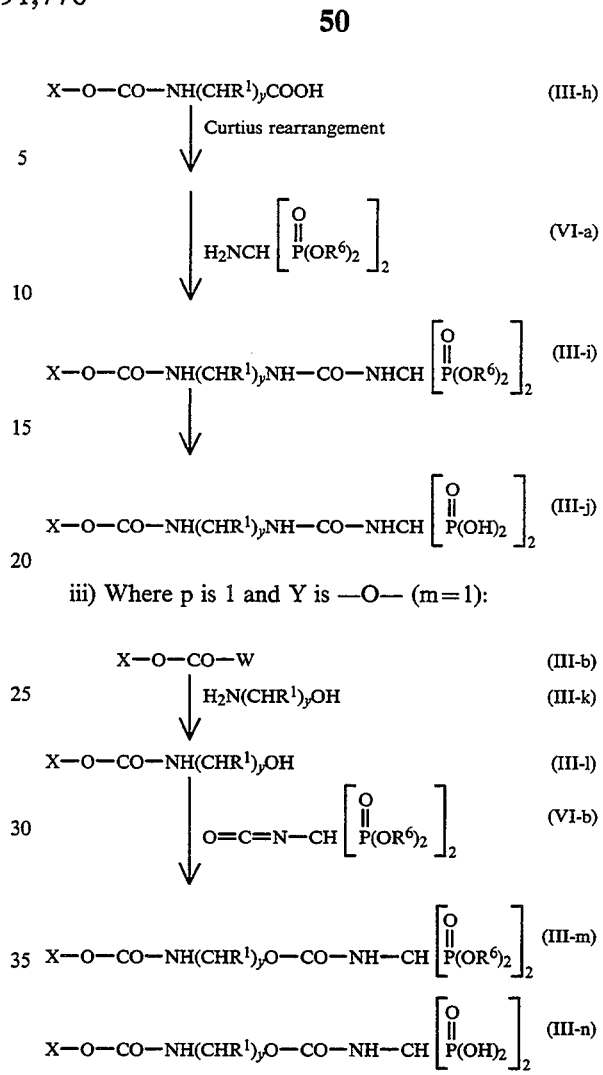

iii) Where p is 1 and Y is —O— (m=1):

In the above formulae, X—O—, $R^1$, y and m have the same meanings as defined in the general formula (I), W represents halogen atom or imidazolyl group, and $R^5$ and $R^6$ each independently represent $C_1$–$C_4$ lower alkyl group.

i) Where p is 0:

Compound (III-b) can be prepared by reacting Compound (II) with Compound (III-a) in an appropriate solvent and, if necessary, in the presence of an appropriate base. The solvent to be used illustratively includes diethyl ether, tetrahydrofuran, dioxane, dimethoxyethane, sulforane, dimethyl sulfoxide, dimethylformamide and the like, and the base to be used includes triethylamine, diisopropylamine, pyridine, collidine, N-methylmorpholine, diazabicycloundecene and the like. The reaction is preferably effected by reacting Compound (II) with 1 to 4 mol equivalent of Compound (III-a) in the presence of 1 to 4 mol equivalent of a base. The reaction is effected usually at temperature from 0° to 150° C., preferably from 20° to 120° C., over a period of 1 to 10 hours.

Compounds (III-d) can be prepared by reacting Compound (III-b) with Compound (III-c) or their salts in an appropriate solvent in the presence of an appropriate base. The solvent illustratively includes diethyl ether, tetrahydrofuran, dioxane, dimethoxyethane, sulforane, dimethyl sulfoxide, dimethylformamide and the like, and the base includes triethylamine, diisopropylamine, pyridine, collidine, N-methylmorpholine, diazabicycloundecene and the like. The reaction is preferably effected by reacting Compound (III-b) with 1 to 4 mol equivalents of Compound (III-c) or their salts in the presence of 2 to 8 mol equivalents of a base. This reaction is carried out usually at temperature from 0° to 150° C., preferably 20° to 120° C., over a period of 10 to 100 hours.

Compound (III-e) or its salt can be prepared by hydrolyzing Compound (III-d) with an aqueous solution of an inorganic base in an appropriate solvent or by deprotecting Compound (III-d) (in which $R^5$=benzyl group or the like) over palladium catalyst in an appropriate solvent. The solvent to be used includes conventional alkanols (e.g. methanol, ethanol, propanol, 2-propanol, butanol, isobutanol, 2-methoxyethanol, etc.), dimethyl sulfoxide, dimethylformamide, and the like. The inorganic base to be used includes sodium hydroxide, potassium hydroxide, lithium hydroxide, calcium hydroxide, barium hydroxide, sodium carbonate, potassium carbonate and the like. Preferable amount of the base used in the reaction is 0.1 to 10 mol equivalents. This reaction is carried out usually at temperature from 20° to 100° C over a period of 1 to 50 hours.

Compound (III-f) can be prepared by reacting Compound (III-e) or its salt with carboxylic acid activator (e.g. dicyclocarbodiimide, isobutyl chloroformate, N,N'-carbonyldiimidazole, thionyl chloride, oxalyl chloride, etc.) in the presence of an appropriate base in an appropriate solvent for activating the carboxyl group of Compound (III-e) and adding tetraalkyl aminomethylenebisphosphonate (VI-a) to the reaction mixture. The solvent to be used illustratively includes dichloromethane, chloroform, diethyl ether, diisopropyl ether, tetrahydrofuran, dioxane, dimethoxyethane, and the like, and the base to be used includes pyridine, collidine, triethylamine, diisopropylethylamine, n-methylmorpholine, diazabicy-cloundecene, and the like. The present reaction is effected by activating carboxyl group of Compound (III-e) with 1 to 2 mol equivalents of a carboxylic acid activator in the presence of 1 to 4 mol equivalents of a base and then adding thereto 1 to 4 mol equivalents of tetraalkyl aminomethylenebisphosphonate. This reaction is preferably effected usually at temperature from −70° to 20° C., preferably −20° to 0° C., over a period of 0.5 to 10 hours.

The compound wherein n equals 0 can be prepared from Compound (III-b) and Compound (VI-a) under conditions employed in the above-mentioned reaction between Compound (III-b) and Compound (III-c).

ii) Where p is 1 and Y is —NH—:

Several methods for converting the carboxyl group of Compound (III-h) or its salt to isocyanate group are known. For example, Compound (III-i) can be prepared by treating Compound (III-h) with DPPA (Diphenyl phosphonoazide) in the presence of an appropriate base and an appropriate solvent for Curtius rearrangement to prepare the isocyanate and then adding tetraalkyl aminomethylenebisphosphonate (VI-a) to the resultant product. The solvent to be used illustratively includes toluene, dioxane, dichloromethane, dimethoxyethane and the like, and the base includes triethylamine, pyridine, diisopropylethy-lamine, N-methylmorpholine, and the like. This reaction is preferably effected by reacting Compound (III-h) with 1 to 2 mol equivalents of DPPA in the presence of 1 to 4 mol equivalents of a base and adding 1 to 4 mol equivalents of tetraalkyl aminomethylenebisphosphonate to the resulting isocyanate. This reaction is carried out usually at temperature from −30° to 200° C., preferably 0° to 130° C.

The compound wherein m is an integer of 2–5 can be prepared in accordance with the above-mentioned preparation employed for the compound wherein m is 1.

iii) Where Y is —O—:

The compound having the above general formula (III-1) or its salt can be prepared from Compound (III-b) and (III-k) in the same manner as the preparation of Compound (III-d) described in the above item i).

Compound (III-m) can be prepared by reacting Compound (III-1) or its salt with Compound (IV-b) in the presence of an appropriate base and an appropriate solvent. The solvent to be used illustratively includes toluene, dioxane, dichloromethane, dimethoxyethane, and the like, and the base includes triethylamine, pyridine, diisopropylethy-lamine, N-methylmorpholine, and the like. The present reaction is preferably effected by reacting Compound (III-1) with 1 to 2 mol equivalents of Compound (IV-b) in the presence of 0 to 4 mol equivalents of a base. This reaction is carried out ordinarily at temperature from −30° to 200° C., preferably 0° to 130° C.

Compounds (III-g), (III-j) and (III-n) can be prepared by respectively reacting Compounds (III-f), (III-i) and (III-m) with trimethylsilane halide in the presence of an appropriate solvent, and then by hydrolyzing the resultant product with water. The solvent to be used illustratively includes tetrahydrofuran, dioxane, dimethoxyethane, acetonitrile and the like, and the trimethylsilane halide includes trimethylsilane iodide, trimethylsilane bromide, trimethylsilane chloride and the like. In the present reaction preferably 4 to 8 mol equivalents of trimethylsilane halide with respect to Compounds (III-f) (III-i) and (III-m) may be used. This reaction is carried out at temperature from −50° to 20° C., preferably −20° to 0° C., over a period of 0.5 to 5 hours.

The compound wherein m is an integer of 2–5 can be prepared in accordance with the above-mentioned preparation employed for the compound wherein m is 1.

(2) Compounds (V-e), (V-g), and (V-1), in which —A— in the general formula (I) represents

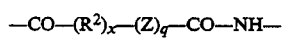

wherein x, $R^2$, Z and q have the same meanings as defined in the general formula (I), or their salts can be prepared in the manner as shown in the following synthetic route.

i) Where q=0:

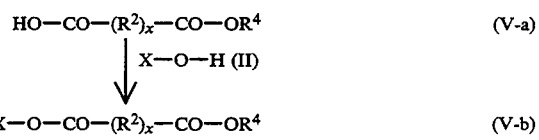

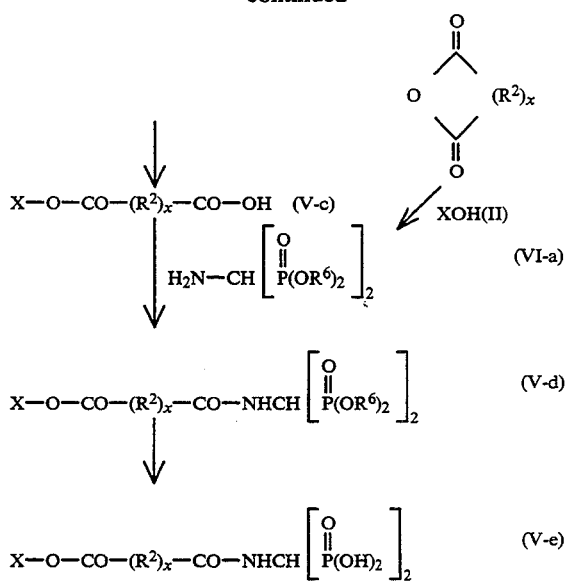

ii) Where Z is —NH— and q=1:

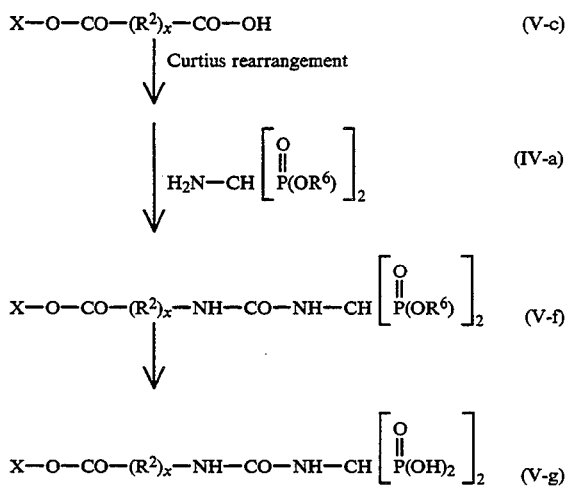

iii) Where Z is —O— and q=1:

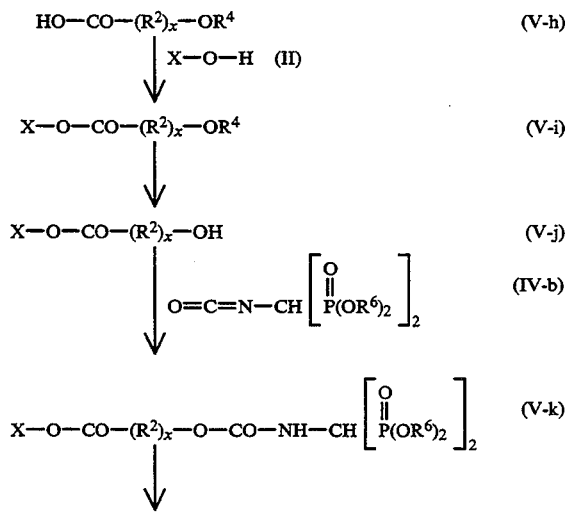

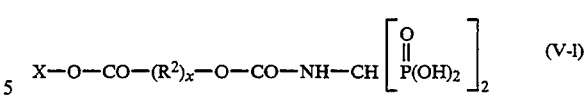

In the above formulae, X—O—, x, $R^2$, Z and q have the same meanings as defined in the general formula (I), and $R^4$ and $R^6$ each independently represent $C_1$–$C_4$ lower alkyl group or benzyl group.

i) Where q=0:

Compounds (V-b) can be prepared by reacting respectively the carboxylic acids (V-a) with a carboxylic acid activator (e.g. dicyclocarbodiimide, isobutyl chloroformate, N,N'-carbonyldiimidazole, thionyl chloride, oxalyl chloride, etc.) in an appropriate solvent for activating the carboxy group and then adding Compound (II) and an appropriate base to the reaction mixture. The solvent to be used illustratively includes dichloromethane, chloroform, diethyl ether, diisopropyl ether, tetrahydrofuran, dioxane, dimethoxyethane and the like, and the base to be used includes pyridine, collidine, triethylamine, diisopropylethylamine, N-methylmorpholine, diazabicycloundecene and the like. The present reaction is preferably effected by treating respectively Compound (V-a) with 1 to 2 mol equivalents of a carboxylic acid activator for activating the carboxy group and then adding to the resulting mixture 1 to 2 mol equivalents of Compound (II) and 1 to 4 mol equivalents of a base. This reaction is carried out usually at temperature from −20° to 100° C., preferably 0° to 80° C., over a period of 0.5 to 10 hours.

Compounds (V-c) or their salts can be prepared by hydrolyzing Compound (V-b) with aqueous solution of an inorganic base in an appropriate solvent or by hydrogenating Compounds (V-b) ($R^4$=benzyl group) over palladium catalyst in an appropriate solvent. Said solvent ordinarily includes alkanols (e.g. methanol, ethanol, propanol, 2-propanol, butanol, isobutanol, 2-methoxyethanol, etc.), dimethyl sulfoxide, dimethylformamide and the like. The inorganic base to be used includes sodium hydroxide, potassium hydroxide, lithium hydroxide, calcium hydroxide, barium hydroxide, sodium carbonate, potassium carbonate and the like. Preferred amount of the base is 0.1 to 10 mol equivalents. The reaction is effected usually at temperature from 20° to 100° C. over a period of 1 to 100 hours. Alternately, Compound (V-c) or its salt can be prepared by treating Compound (II) with 1 to 6 mol equivalents of acid anhydride (V-a') in the presence of a base. The solvent to be used includes organic amines (e.g. pyridine, collidine, etc.), toluene, dioxane and the like. The base includes triethylamine, pyridine, 4-dimethylaminopyridine, and the like.

Compound (V-d) can be prepared by reacting Compound (V-c) or its salt with a carboxylic acid activator (e.g. dicyclocarbodiimide, isobutyl chloroformate, N,N'-carbonyldiimidazole, thionyl chloride, oxalyl chloride, etc.) in the presence of an appropriate base in an appropriate solvent for activating the carboxy group of Compound (V-c) and then adding to the resulting mixture tetraalkyl aminomethylenebis-phosphonate (VI). The solvent to be used illustratively includes dichloromethane, chloroform, diethyl ether, diisopropyl ether, tetrahydrofuran, dioxane, dimethoxyethane and the like, and the base to be used includes pyridine, collidine, triethylamine, diisopropylethylamine, N-methylmorpholine, diazabicycloundecene, etc. The present reaction is preferably effected by adding 1 to 2 mol equivalents of a carboxylic acid activator and 1 to 4 mol equivalents of a base to Compound (V-c) for activating the carboxy group of Compound (V-c) and then adding 1 to 4 mol equivalents of tetraalkyl aminomethylenebisphosphonate. This reaction is carried out usually at temperature from −70° to 20° C., preferably −20° to 0° C., over a period of 0.5 to 10 hours.

ii) Where Z=—NH— and q=1:

Compound (V-f) can be prepared, for example, by subjecting Compound (V-c) or its salt to Curtius rearrangement with DPPA (diphenyl phosphonoazide) in the presence of an appropriate base and an appropriate solvent and then reacting the resulting isocyanate with tetraalkyl aminomethylenebisphosphonate (VI-a). The solvent to be used includes toluene, dioxane, dichloromethane, dimethoxyethane, and the like. The base to be used includes triethylamine, pyridine, diisopropylethylamine, N-methylmorpholine and the like. The present reaction is preferably effected by adding 1 to 2 mol equivalents of DPPA and 1 to 4 mol equivalents of a base to Compound (V-c) and then adding 1 to 4 mol equivalents of tetraalkyl aminomethy-lenebisphosphonate. This reaction is carried out usually at temperature from −30° to 200° C., preferably 0° to 130° C.

iii) Where Z=—O— and q=1:

The compound having the above .general formula (V-j) or its salt can be prepared from Compound (V-h) and Compound (II) via Compound (V-i) in the same manner as the preparation of Compound (V-c) described in the above item i).

Compound (V-k) can be prepared by reacting Compound (V-j) or its salt with an appropriate base in an appropriate solvent. The solvent to be used illustratively includes toluene, dioxane, dichloromethane, dimethoxyethane and the like, and the base to be used includes triethylamine, pyridine, diisopropylethylamine, N-methylmorpholine and the like. In the present reaction, 1 to 2 mol equivalents of Compound (IV-b) and 0 to 4 mol equivalents of a base with respect to Compound (V-j) are preferably used. This reaction is carried out usually at −30° to 200° C., preferably 0° to 130° C.

Compounds (V-e), (V-g) and (V-1) can be prepared by reacting respectively Compounds (V-d), (V-f) and (V-k) with a trimethylsilane halide in an appropriate solvent and then hydrolyzing the resultant product with water. The solvent to be used includes tetrahydrofuran, dioxane, dimethoxyethane, acetonitrile and the like, and the trimethylsilane halide includes trimethylsilane iodide, trimethylsilane bromide, trimethylsilane chloride and the like. In the present reaction, 4 to 8 mol equivalents of trimethylsilane halide is used for one mol of Compounds (V-d), (V-f) and (V-k). This reaction is carried out usually at temperature from −50° to 20° C., preferably −20° to 0° C., over a period of 0.5 to 5 hours.

(3) Compound (VI-c) in which -A- in the general formula (I) represents

—CO—(CH$_2$)$_n$— wherein n has the same meaning as defined in the general formula (I), or its salt can be prepared according to the following synthetic route:

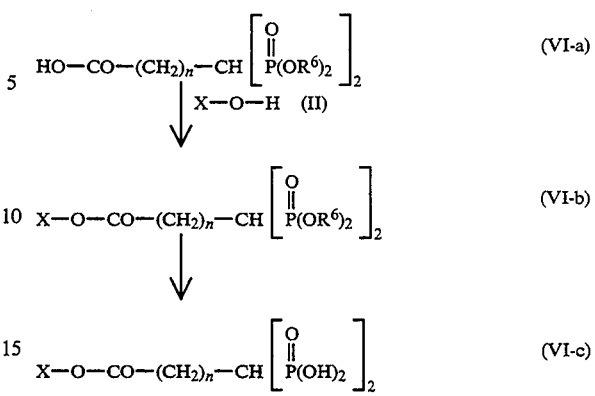

In the above formulae, X—O— and n have the same meanings as defined in the general formula (I), and R$^6$ represents C$_1$–C$_4$ lower alkyl group.

Compound (VI-b) can be prepared by reacting the carboxylic acid (VI-a) with a carboxylic acid activator (e.g. dicyclocarbodiimide, isobutyl chloroformate, N,N'-carbonyldiimidazole, thionyl chloride, oxalyl chloride, etc.) in an appropriate solvent for activating the carboxyl group of Compound (VI-a) and then adding to the resultant mixture Compound (II) and an appropriate base. The solvent to be used illustratively includes dichloromethane, chloroform, diethyl ether, diisopropyl ether, tetrahydrofuran, dioxane, dimethoxyethane, and the like, and the base to be used includes pyridine, collidine, triethylamine, diisopropylethylamine, N-methylmorpholine, diazabicycloundecene, and the like. In the present invention, preferably 1 to 2 mol equivalents of a carboxylic acid activator is added to Compound (VI-a) for activating the carboxy group, and then 1 to 2 mol equivalents of Compound (II) and 1 to 4 mol equivalents of a base are added. This reaction is carried out usually at temperature from −20° to 100° C., preferably 0° to 80° C., over a period of 0.5 to 10 hours.

Compound (VI-c) can be obtained by reacting Compound (VI-b) with a trimethylsilane halide in an appropriate solvent and hydrolyzing the resultant product with water. The solvent to be used illustratively includes tetrahydrofuran, dioxane, dimethoxyethane, acetonitrile and the like, and the trimethylsilane halide includes trimethylsilane iodide, trimethylsilane bromide, trimethylsilane chloride and the like. In the present reaction, preferably 4 to 8 mol equivalents of trimethylsilane halide is added to Compound (VI-b). This reaction is carried out usually at temperature from −50° to 20° C., preferably −20° to 0° C., over a period of 0.5 to 5 hours.

The present invention will be explained in more detail by way of the following Preparations and Examples, but the scope of the present invention should not be construed to be limited to those Preparations and Examples.

Preparation 1

17β-Imidazolylcarbonyloxy-3-methoxymethyloxy-1,3,5-estratriene

To a solution of 17β-hydroxy-3-methoxymethyloxy-1,3,5-estratriene (3.34 g) in dioxane (70 ml) were added N,N'-carbonyldiimidazole (4.30 g) and triethylamine (3.3 ml), and the resultant mixture was refluxed under heating and stirring for 3 hours. After cooling, the reaction mixture was mixed with water and extracted with ethyl acetate. The organic layer was washed with saturated saline, dried over anhydrous magnesium sulfate, and the solvent was evaporated. The residue was chromatographed on a silica gel column (120 g), eluting with hexane-ethyl acetate to give 17β-imidazolylcarbonyloxy-3-methoxymethyloxy-1,3,5-estratriene (3.56 g, Yield: 82%).

NMR (CDCl$_3$, δ) 8.14 (1H, s), 7.42 (1H, 2), 7.20 (1H, d, J=8.5Hz), 7.08 (1H, s), 6.84 (1H, dd, J=7.7Hz, 7.7Hz), 3.47 (3H, s), 2.86 (2H, m), 0.94 (3H, s)

Preparation 2

17β-Methoxycarbonylmethylaminocarbonyloxy-3-methoxy-methyloxy-1,3,5-estratriene

To a solution of 17β-imidazolylcarbonyloxy-3-methoxymethyloxy-1,3,5-estratriene (1.14 g) in dioxane (25 ml) were added glycine methyl ester hydrochloride (1.05 g), triethylamine (1.16 ml), and diazabicycloundecene (1.25 ml). The resultant mixture was refluxed under heating and stirring for 3 days. After cooling, the reaction mixture was mixed with water and extracted with ethyl acetate. The organic layer was washed with saturated saline, dried over anhydrous magnesium sulfate, and the solvent was evaporated. The residue was chromatographed on a silica gel column (100 g), eluting with hexane-ethyl acetate to give 17β-methoxycarbonylmethylaminocarbonyloxy-3-methoxymethyloxy-1,3,5-estratriene (0.77 g, Yield: 64%).

NMR (CDCl$_3$, δ) 7.20 (1H, d, J=8.5Hz), 6.83 (1H, dd, J=8.5 Hz, 2.5 Hz), 6.77 (1H, d, J=2.5 Hz), 5.14 (3H, s), 4.65 (1H, dd, J=7.7Hz, 7.7Hz), 3.98 (2H, d, J=5.5Hz), 3.77 (2H, 3H), 3.47 (3H, s), 2.90–2.82 (2H, m), 0.81 (3H, s)

Preparation 3

17β-[(2-Methoxycarbonylethyl)aminocarbonyloxy]-3-methoxymethyloxy-1,3,5-estratriene The reaction was effected in the same manner as in Preparation 2 except that β-alanine methyl ester hydrochloride was used in place of glycine methyl ester hydrochloride, whereby 17β-[(2-methoxycarbonylethyl)aminocarbonyloxy]-3-methoxymethyloxy-1,3,5-estratriene was obtained. Yield: 87%.

NMR (CDCl$_3$, δ) 7.20 (1H, d, J=8.5Hz), 6.82 (1H, dd, J=2.5Hz, 8.5Hz), 6.77 (1H, d, J=2.5Hz), 5.14 (1H, s), 4.62 (1H, t, J=8.2Hz), 3.71 (3H, s), 3.47 (3H, s), 3.47–3.40 (2H, m), 2.84 (2H, t, J=4.3Hz), 2.56 (2H, t, J=6.0Hz), 0.78 (3H, s)

Preparation 4

17β-Carboxymethylaminocarbonyloxy-3-methoxymethyloxy-1,3,5-estratriene

To a solution of 17β-methoxycarbonylmethylaminocarbonyloxy-3-methoxymethyloxy-1,3,5-estratriene (0.77 g) in methanol (40 ml) was added 2 N aqueous potassium hydroxide (6 ml), and the resultant mixture was stirred at room temperature for 2 hours. The reaction mixture was mixed with ion exchange resin (DOWEX, 5W-X8), neutralized, and filtered to remove the ion exchange resin. The filtrate was concentrated in vacuo to give 17β-carboxymethylaminocarbonyloxy-3-methoxymethyloxy-1,3,5-estratriene (0.65 g, Yield: 88%) as an amorphous solid.

NMR (DMSOd-6, δ) 7.16 (1H, d, J=8.5Hz), 6.75 (1H, dd, J=8.5Hz, 2.5Hz), 6.69 (1H, d, J=2.5Hz), 5.10 (2H, s), 4.45 (1H, t, J=8.5Hz), 3.33 (3H, s), 3.22 (2H, d, J=4.3Hz), 2.84–2.74 (2H, m), 0.76 (3H, s)

Preparation 5

17β-[(2-Carboxyethyl)aminocarbonyloxy]-3-methoxymethyloxy-1,3,5-estratriene

17β-[(2-Methoxycarbonylethyl)aminocarbonyloxy]-3-methoxymethyloxy-1,3,5-estratriene obtained in Preparation 3 was treated in the same manner as in Preparation 4 to give 17η-[(2-Carboxyethyl)aminocarbonyloxy]-3-methoxymethyloxy-1,3,5-estratriene. Yield: 85%.

NMR (DMSOd-6) 7.16 (1H, d, J=8.5Hz), 7.04 (1H, t, J=5.0Hz), 6.75 (1H, dd, J=2.5Hz, 8.5Hz), 6.69 (1H, d, J=2.5Hz), 5.10 (2H, s), 4.47 (1H, t, J=8.2Hz), 3.33 (3H, s), 3.16 (2H, dt, J=5.0Hz, 7.6Hz), 2.83–2.73 (2H, m), 2.37 (2H, t, J=7.6Hz), 0.75 (3H, s)

Preparation 6

17β-[3-Methoxymethyloxy-1,3,5-estratriene]hemisuccinate

To a solution of 17β-hydroxy-3-methoxymethyloxy-1,3,5-estratriene (3.65 g) and succinic anhydride (6.9 g) in toluene (54 ml) were added pyridine (9.3 ml) and 4-dimethyl-aminopyridine (140 mg), and the resultant mixture was refluxed under heating for 48 hours. The reaction mixture was washed with saturated aqueous potassium bisulfate, and the organic layer was concentrated to give a brown oil. This was chromatographed on a silica gel column (300 g), eluting with chloroform-/methanol to give 17β-[3-methoxy-methyloxy-1,3,5-estratriene]hemisuccinate (3.0 g, Yield: 63%) as a colorless oil.

NMR (CDCl$_3$, δ) 7.19 (d, 1H, 8.6Hz), 6.82 (33, 1H, 8.6Hz, 2.7Hz), 6.77 (d, 1H, 2.7Hz), 5.14 (s, 2H), 4.71 (t, 1H, 7.6Hz), 3.47 (s, 3H), 2.9–2.8 (m, 2H), 2.3–1.1 (m, 13H), 0.82 (s, 3H)

Preparations 7–12

The following compounds were prepared according to Preparation 6, using other anhydrides or steroids than used in Preparation 6.

Preparation 7

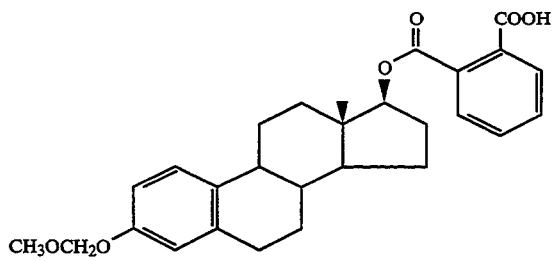

Yield: 64% NMR (CDCl$_3$, δ) 7.90–7.83 (m, 1H), 7.75–7.70 (m, H), 7.65–7.50 (m, 2H), 7.14 (d, 1H, 8.6Hz), 6.82–6.70 (m, 2H), 5.12 (s, 2H), 4.92 (t, 1H, 7.4Hz), 3.45 (s, 3H), 2.90–2.75 (m, 2H), 2.45–2.10 (m, 3H), 2.05–1.62 (m, H), 1.55–1.20 (m, 6H), 0.85 (s, 3H)

Preparation 8

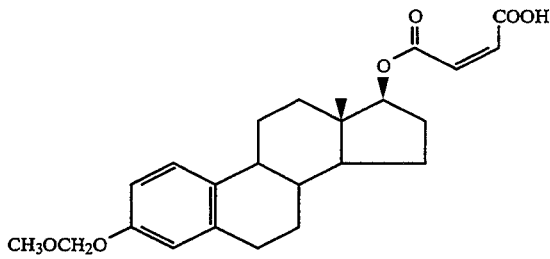

Yield: 25% NMR (CDCl₃ δ) 7.17 (d, 1H, 8.6Hz), 6.81 (dd, 1H, 2.7Hz, 8.6Hz), 6.76 (d, 1H, 2.7Hz) 6.47 (d, 1H, 12.9Hz), 6.38 (d, 1H, 12.9Hz), 5.13 (x, 2H), 4.82 (t, 1H, 7.4Hz), 3.45 (s, 3H), 2.90-2.78 (2H, m), 2.88-2.78 (m, 2H), 2.38-2.10 (m, 3H), 1.98-1.25 (m, 10H), 0.85 (s, 3H).

Preparation 2

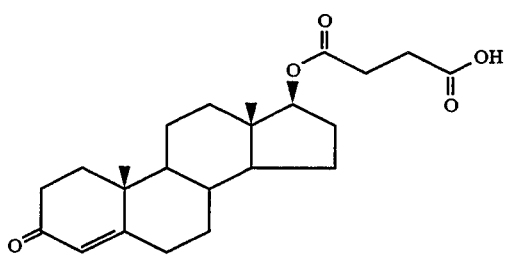

Yield: 74% NMR (CDCl₃, δ) 5.71 (s, 1H), 4.60 (t, 1H, 7.6Hz), 2.70-2.50 (m, 4H), 2.50-0.93 (m, 19H), 1.16, 0.80 (each: s, 3H).

Preparation 10

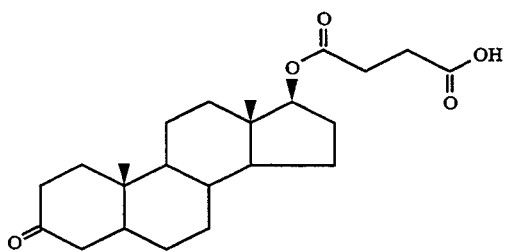

Yield: 36 % NMR (CDCl₃, δ) 460 (t, 1H, 7.6Hz), 2.70-2.58 (m, H), 2.20-1.90 (m, 6H), 1.75-0.70 (m, 16H), 0.99, 0.78 (each: s, 3H).

Preparation 11

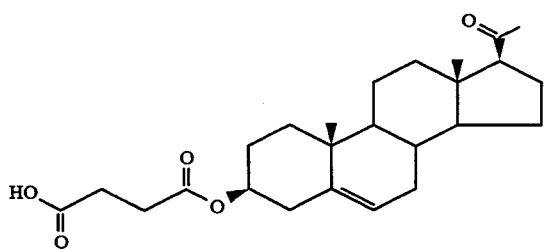

Yield: 70% NMR (CDCl₃, δ) 5.35 (d, 1H, 4.3Hz), 4.66-4.50 (m, H), 2.70-2.44 (m, 5H), 2.40-0.95 (m, 19H), 2.10, 0.99, 0.60 (each: s, 3H)

Preparation 12

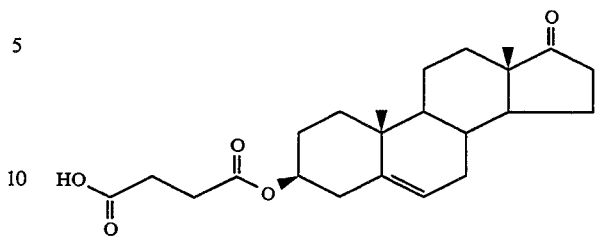

Yield: 60% NMR (CDCl₃, δ) 5.38 (d, 1H, 4.8Hz), 4.7-4.5 (m, H), 2.70-2.50 (m, 4H), 2.50-2.22 (m, 3H), 2.15-1.75 (m, 6H), 1.70-0.95 (m, 11H), 1.02, 0.86 (each: s, 3H)

Preparation 13
17-Oxo-3-(2'-carboxyethyl)aminocarbonyloxy-1,3,5-estratriene To a solution of succinic acid monobenzyl ester (571 mg) in toluene (5.7 ml) was added triethylamine (458 ml), and the resultant mixture was chilled at 0° C., gradually mixed with DPPA (620 μl), and stirred at 100° C. for 30 minutes. After confirming that generation of gas was finished, the reaction mixture was chilled at 0° C., mixed dropwise with a solution of 3-hydroxy-17-oxo-1,3,5-estratriene (740 mg) in toluene (7.4 ml), and stirred at 100° C. for 1 hour. The reaction mixture was allowed to cool to room temperature, diluted with chloroform, washed with water, and then concentrated. The residue was chromatographed on a silica gel column, eluting with chloroform/methanol to give 343 mg of colorless crystals.

To a solution of said product in ethanol (3.4 ml)/tetrahydrofuran (3.4 ml) was added 10% palladium carbon (34 mg), and the resultant mixture was hydrogenated for 1 hour. The reaction mixture was filtered with Celite, and the filtrate was concentrated to give 17-oxo-3-(2'-carboxyethyl)aminocarbonyloxy-1,3,5-estratriene (231 mg) as colorless crystals. Yield: 29%.

NMR (CDCl₃) 7.66 (br-s, 1H) 7.23 (d, 1H, 85Hz), 6.90-6.80 (m, 3H), 5.62 (t, 1H, 6.2Hz), 3.60-3.40 (m, 2H), 2.95-2.80 (m, 2H), 2.15-2.60 (m, 2H), 2.50-1.90 (m, 7H), 1.70-1.30 (m, 6H), 0.88 (s, 3H).

Preparation 14
[17β-(3-Methoxymethyloxy-1,3,5-estratrienyloxy)carbonylaminomethylcarboxamidomethylene]bis(phosphonate)tetraethyl To a solution of 17β-carboxymethylaminocarbonyloxy-3-methoxymethyloxy-1,3,5-estratriene (0.65 g) in tetrahydrofuran (20 ml) obtained in Preparation 4 was added N-methylmorpholine (0.19 ml), and the resultant mixture was chilled at −10° C., gradually added with isobutyl chloroformate (0.22 ml), and stirred at −10° C. for 15 minutes. A solution of tetraethyl aminomethylenebisphosphonate (0.47 g) in tetrahydrofuran (5 ml) was added at −10° C. to the mixture, which was stirred for 30 minutes. The reaction mixture was diluted with ethyl acetate, and washed with water and saturated saline. The organic layer was dried over anhydrous magnesium sulfate, and concentrated to remove the solvent. The residue was chromatographed on a silica gel column (30 g), eluting with chloroform/methanol to give [17β-(3-methoxymethyloxy-1,3,5-estratrienyloxy) carbonyl-aminomethylcarboxamidomethylene]bis(phosphonate)tetraethyl (910 mg). Yield: 84%.

NMR (CDCl₃, δ) 7.19 (1H, d, J=8.5Hz), 7.13 (1H, d, J=8.4Hz), 6.82 (1H, dd, J=2.5Hz, 8.5Hz), 6.77 (1H, d, J=2.5Hz), 5.46 (1H, J=4.9Hz), 5.14 (2H, s), 5.04 (1H, dt, J=10Hz, 22 Hz), 4.62 (1H, t, J=8.4Hz), 4.28 - 4.13 (8H, m), 3.97 (2H, d, J=4.9Hz), 3.47 (s, 3H), 2.84 (2H, t, J=4.4Hz), 1.39-1.30 (15H, m), 0.81 (3H, s)

Preparations 15-28

Using steroidal carboxylic acid derivatives already known or the steroidal carboxylic acid derivatives obtained above as starting materials, the reactions were carried out in the same manner as in Preparation 14 to give the compounds having the following general formula.

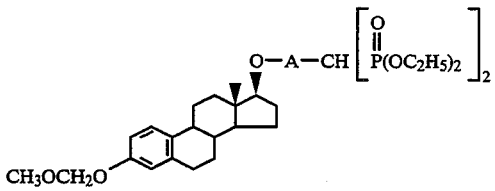

Preparation 15

Yield: 71% NMR (CDCl₃, δ) 7.19 (1H, d, J=B.5Hz), 6.82 (1H, dd, J=2.5Hz, 8.5Hz), 6.77 (1H, d, J=2.5Hz), 6.42 (1H, d, J=10.0Hz), 5.44 (1H, t, J=2.5Hz), 5.14 (2H, s), 5.03 (1H, dt, J=10.0Hz, 21.7Hz), 4.61 (1H, t, J=8.3Hz), 4.24–4.13 (m, 8Hz), 3.54–3.40 (2H, m), 3.47 (s, 3H), 2.84 (2H, t, J=4.3Hz), 2.51 (2H, t, J=5.6Hz), 1.35 (6H, t, J=7.1Hz), 1.34 (6H, t, J=7.1Hz), 0.77 (3H, s).

Preparation 16

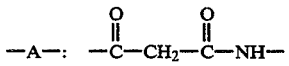

Yield: 6.3% NMR (CDCl₃, δ), 7.62 (d, 1H, J=10.0Hz), 7.19 (d, 1H, J=8.5Hz), 6.83 (dd, 1H, J=2.5Hz, 8.5Hz), 6.77 (d, 1H, J=2.5Hz), 5.14 (s, 2H), 5.05 (Dt, 1H, J=21.5Hz, 10.0Hz), 4.75 (t, 1H, 8.8Hz), 4.25–4.16 (m, 8H), 3.47 (s, 3H), 3.40 (s, 2H) 2.84 (t, 2H, J=4.5Hz), 2.29-2.20 (m, 3H), 1.91-1.31 (m, 22H), 0.83 (s, 3H)

Preparation 17

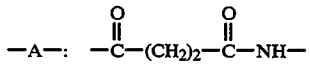

Yield: 97% NMR (CDCl₃, δ), 7.20 (d, 1H, J=8.6Hz), 6.83 (dd, 1H, J=2.5Hz, 8.6Hz), 6.78 (d, 1H, J=2.5Hz), 6.36 (d, 1H, J=10.0Hz), 5.15 (s, 2H), 5.03 (dt, 1H, J=10.0Hz, 21.8Hz) 4.69 (t, 1H, J=7.8Hz), 4.24–4.14 (m, 8H) 3.47 (s, 3H) 2.80-2.83 (m, 2H), 2.71-2.59 (m, 4H), 2.31-2.16 (m, H), 1.90-1.09 (m, 10H), 1.34 (t, 12H, J=7.1Hz), 0.82 (s, 3H)

Preparation 18

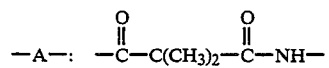

Yield: 100% NMR (CDCl₃, δ), 7.16 (d, 1H, 8.6Hz) 7.13 (d, 1H, 10Hz), 6.79 (dd, 1H, 2.5Hz, 8.6Hz), 6.74 (d, 1H, 2.5Hz), 5.11 (5.2H), 5.00 (dt, 1H, 10Hz, 21.8Hz), 4.70 (t, 1H, 7.8Hz), 4.30–4.25 (m, 8H), 3.44 (s, 3H), 2.90-2.76 (m, 2H) 2.40-2.05 (m, 3H), 1.95-1.10 (m, 10H), 1.47, 1.46 (each s, each 3H), 1.32 (t, 12H, J=7.1Hz), 0.83 (s, 3H)

Preparation 19

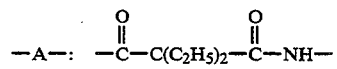

Yield: 13% NMR (CDCl₃, δ) 8.96 (d, 1H, 9.8Hz) 7.14 (d, 1H, 8.6Hz), 6.79 (dd, 1H, 8.6Hz, 2.6Hz), 6.73 (d, 1H, 2.6Hz), 5.12 (dt, 1H, 10Hz, 21.8Hz), 5.10 (5.2H), 4.73 (t, 1H, 7.8Hz), 4.30–4.10 (m, 8H), 3.43 (s, 3H), 2.90–2.75 (m, H) 2.40-1.20 (m, 17H), 1.32 (t, 12H, 7.1Hz), 0.90-0.75 (m, 9H).

Preparation 20

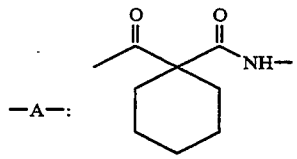

Yield: 38% NMR (CDCl₃, δ), 7.17 (d, 1H, 8.6Hz), 6.80 (dd, 1H, 2.5Hz, 8.6Hz), 6.52 (d, 1H, 10Hz), 5.12 (s, 2H), 4.97 (dt, 1H, 10Hz, 21.8Hz), 4.71 (t, 1H, 7.8Hz), 4.15–4.05 (m, 8H), 3.45 (s, 3H), 2.90–2.78 (m, 2H), 2.40–2.05 (m, H), 2.00-1.20 (m, 14H), 1.32 (t, 12H, J=7.1Hz), 0.85 (s, 3H)

Preparation 21

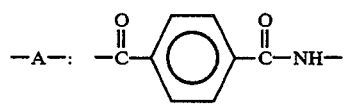

Yield: 33% NMR (CDCl₃, δ), 8.11, 7.86 (each: d, 2H, 8.4Hz), 7.18 (d, 1H, 8.6Hz), 6.9–6.7 (m, 3H), 5.23 (dt, 1H, 10Hz, 21.8Hz), 5.13 (s, 2H), 4.93 (t, 1H, 7.8Hz), 4.40–4.10 (m, 12H), 3.45 (s, 3H), 2.90–2.80 (m, 2H), 2.5–2.2 (m, 3H), 2.0–1.2 (m, 22H), 0.95 (s, 3H).

Preparation 22

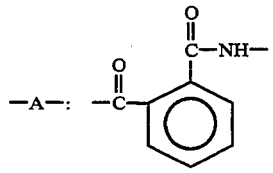

Yield: 53% NMR (CDCl₃, δ), 7.95-7.90 (m, 1H), 7.60-7.45 (m, 3H), 7.18 (d, 1H, 8.6Hz), 7.80 (dd, 1H, 2.5Hz, 8.6Hz), 6.76 (d, 1H, 2.5Hz), 6.64 (d, 1H, 10Hz), 5.21 (dt, 1H, 10Hz, 21.8Hz), 5.12 (s, 3H), 4.86 (t, 1H, 7.8Hz), 4.40–4.10 (m, 8H), 3.45 (s, 3H), 2.90–2.80 (2H, m), 2.40–2.10 (m, 3H), 2.0–1.7 (m, 22H), 0.91 (s, 3H)

Preparation 23

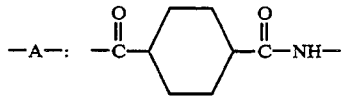

Yield: 29% NMR (CDCl₃, δ), 7.13 (d, 1H, 8.6Hz), 6.76(dd, 1H, 2.7Hz, 8.6Hz), 6.33 (d, 0.5H, 9.2Hz), 6.21 (d, 1H, 9.2Hz), 5.08 (s, 2H), 4.95 (dt, 1H, 10Hz, 21.6Hz), 4.64 (t, 1H, 7.6Hz), 4.3–4.0 (m, 8H), 3.41 (s, 3H), 2.9–2.7 (m, 2H), 2.6–2.4 (m, 1H), 2.3–1.1 (m, 20H), 1.4–1.2 (m, 12H), 0.76 (s, 3H)

Preparation 24

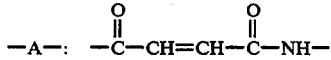

Yield: 48% NMR (CDCl₃, δ), 9.55 (d, 1H, 9.9Hz), 7.17 (d, 1H, 8.6Hz), 6.81 (dd, 1H, 2.7Hz, 8.6Hz), 6.75 (d, 1H, 2.7Hz), 6.32 (d, 1H, 13.2Hz), 6.22 (d, 1H, 13.2Hz), 5.12 (s, 2H), 5.09 (dt, 1H, 21.6Hz, 10Hz), 4.75 (t, 1H, 7.6Hz), 4.3–4.1 (m, 8H), 3.45 (s, 3H), 2.9–2.7 (m, 2H), 2.4–1.2 (m, 13H), 1.4–1.2 (m, 12H), 0.82 (s, 3H)

Preparations 25–28

In the same manner as in Preparations 16–26, the compounds having the following general formula were obtained.

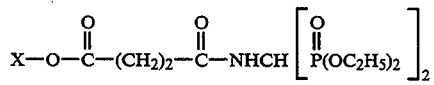

Preparation 25

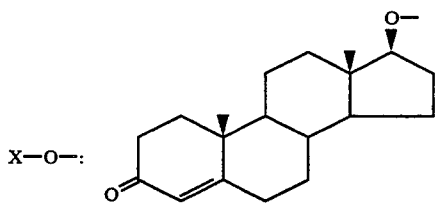

Yield: 84% NMR (CDCl₃, δ), 6.40 (d, 1H, 10Hz), 5.68 (d, 1H, 0.8Hz ), 4.98 ( dt, 1H, 10Hz, 21.8Hz ), 4.55 ( dd, 1H, 7.6Hz, 9.0Hz), 4.3–4.1 (m, 8H), 2.7–2.5 (m, 4H), 2.5–0.9 (m, 19H), 1.29 (t, 12H, 7.1Hz), 1.15 (s, 3H), 0.79 (s, 3H)

Preparation 26

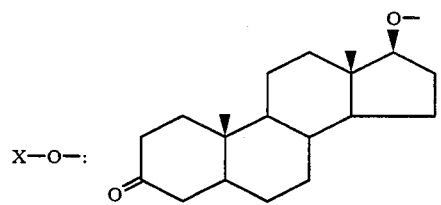

Yield: 67 % NMR (CDCl₃, δ), 6.25 (d, 1H, 10Hz), 4.99 (dt, 1H, 10Hz, 21.8Hz), 4.58 (t, 1H, 7.6Hz), 4.25–4.10 (m, 8H), 2.70–2.50 (m, 4H), 2.40–1.90 (m, 6H), 2.80–0.70 (m, 16H), 0.99, 0.78 (each s, 3H), 1.34 (t, 12H, 6.8Hz)

Preparation 27

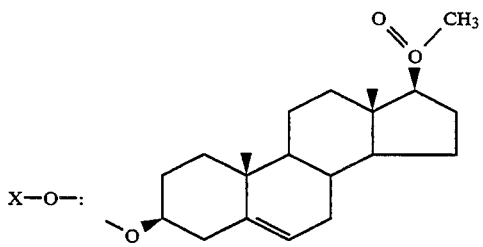

Yield: 74% NMR (CDCl₃, δ), 5.35 (d, 1H, 4.3Hz), 4.5–4.7 (m, 1H), 2.70–2.20 (m, 5H), 2.35–0.95 (m, 19H), 2.10, 0.99, 0.61 ( each s, 3H)

Preparation 28

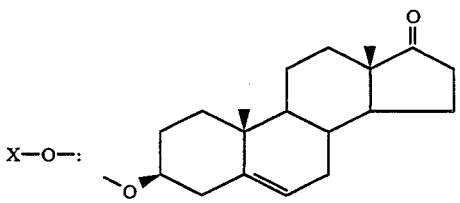

Yield: 65% NMR (CDCl₃, δ), 5.38 (d, 1H, 4.78Hz), 4.7–4.5 (m, H), 2.7–2.5 (m, 4H), 2.50–0.95 (m, 17H), 1.02, 0.86 (each s, 3H)

Preparation 29

{2-[3'-(17'β-Hydroxy-1',3',5'-estratrienenyloxy)carbonylamino]ethylcarboxamidomethylene}bis(phosphonate)tetraethyl Using 17-oxo-3-[2'-(carboxy)ethylaminocarbonyl-]oxy-1,3,5-estratriene (231 mg), the reaction was carried out in the same manner as in Preparation 8 to give light yellow syrup (402 mg). To a solution of this product in methanol (6.0 ml) was added sodium borohydride (34 mg) at 0° C. under stirring, and the resultant mixture was stirred for 30 minutes. The mixture was poured into saturated aqueous ammonium chloride (50 ml) and shaken with chloroform. The organic layer was concentrated, and the residue was chromatographed on a silica gel column, eluting with methanol/water to give the titled compound (242 mg). Yield: 60%.

NMR (CDCl₃, δ) 7.21 (d, 1H, 8.4Hz), 6.81 (dd, 1H, 2.0Hz, 10.4Hz), 6.77 (d, 1H, 2.0Hz), 6.02 (t, 1H, 6.2Hz), 5.04 (dt, 1H, 10.1Hz, 21.8Hz), 4.3–4.1 (m, 8H), 3.69 (t,

H, 8.1Hz), 3.62–3.50 (m, 2H), 2.85–2.70 (m, 2H), 2.60–2.50 (m, 2H), 2.35–1.10 (m, 13H), 1.31 (t, 12H), 0.73 (5.3H)

Preparation 30–32

The reaction was carried out in the same manner as in Preparation 29 to give the compounds having the following general formula.

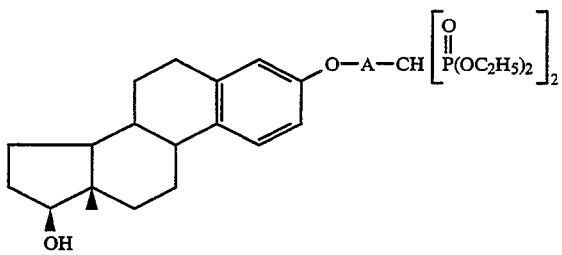

Preparation 30

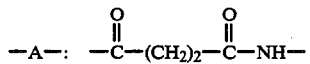

Yield: 52% NMR (CDCl$_2$, δ), 7.24 (d, 1H, 8.6Hz), 6.81 (dd, 1H, 2.6Hz, 8.4Hz), 6.76 (d, 1H, 2.5Hz), 6.28 (d, 8.4Hz), 4.92 (dt, 1H, 10Hz, 21.8Hz), 4.25–4.05 (m, 8H), 3.71 (t, 1H, 8.3Hz), 3.9–3.7 (m, 4H), 2.66 (t, 2H, 5.95Hz), 2.40–1.10 (m, 25H), 0.75 (5.3H)

Preparation 31

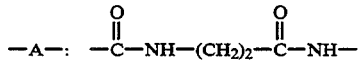

Yield: 60% NMR (CDCl$_2$, δ), 7.90 (d, 9.9Hz), 7.06 (d, 1H, 8.6Hz ), 6.78–6.60 (m, 2H), 6.29 (t, 1H, 5.3Hz), 4.98 (dt, 1H, 10Hz, 22.1Hz ), 4.2–3.95 (m, 8H), 3.50–3.30 (m, 2H) , 2.8–2.6 (m, 2H), 2.50–1.10 (m, 15H), 1.21 (t-like, 12H), 0.73 (s, 3H)

Preparation 32

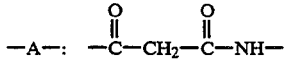

Yield: 25% NMR (CDCl$_3$, δ), 7.62 (d, 10.0Hz), 7.25 (d, 1H, 8.7Hz ) , 6.90–6.70 (m, 2H), 5.05 (dt, 1H, 9.8Hz, 21.6Hz), 4.3–4.1 (m, 8H), 3.70 (t, 1H, 8.3Hz), 3.62 (s, 2H), 2.90–2.70 (m, 1H), 2.40–1.0 (m, 2.5H), 0.75 (s, 3H)

Preparation 33

{2-[3'-(17'β-Acetoxy-1',3',5'-estratrienyloxy)carbonyl-]ethylcarboxamidomethylene}bis(phosphonate)tetraethyl To a solution of {2-[3'-(17'β-hydroxy-1',3',5'-estratrienyloxy)carboxyethyl]carboxamidomethylene}bis(phosphonate)tetraethyl in methylene chloride (2 ml) were added 4-dimethylaminopyridine (23.0 mg) and acetic anhydride (16.7 ml), and the resultant mixture was stirred at room temperature for 1 hour and poured into chilled water. The mixture was shaken with chloroform, and the organic layer was concentrated. The residue was chromatographed on a silica gel column to give the titled compound (82.4 mg).

NMR, 7.20 (d, 1H, 8.6Hz), 6.80–6.65 (m, 2H), 4.97 (dt, 1H, 10Hz, 21.8Hz), 4.63 (t, 1H, 8.3Hz), 4.3–4.0 (m, 8H), 2.90–2.60 (m, 4H), 2.3–2.1 (m, 2H), 2.01 (s, 3H), 1.90–1.20 (m, 27H), 0.77 (s, 3H)

Preparation 34

{2-[3'-(17'β-Cyclohexylcarboxy-1',3',5'-estratrienyloxy)carbonyl]ethylcarboxamidomethylene}bis(phosphonate)tetraethyl The reaction was carried out in the same manner as in Preparation 33 to give the titled compound.

NMR, 7.22 (d, 2H, 8.6Hz), 6.79 (dd, 1H, 2.4Hz, 8.3hz), 6.60–6.40 (m, 1H), 5.02 (dt, 1H, 10Hz, 21.8Hz), 4.66 (t, 1H, 8.3Hz), 4.30–4.00 (m, 8H), 2.90–2.75 (m, 4H), 2.70–2.60 (m, 2H), 2.40–1.20 (m, 32H), 0.80 (s, 3H)

Preparation 35

[17β-(3-Hydroxy-1,3,5-estratrienyloxy)carbonylmethylurein-methylene]bis(phosphonate)tetraethyl To a solution of 17β-[3-methoxymethyloxy-1,3,5-estratriene]hemisuccinate in toluene (2.5 ml) were added triethylamine (127 μl) and DPPA (230 μl), and the resultant mixture was stirred at 100° C. for 30 minutes and poured into chilled water (30 ml). After generation of gas was finished, aminomethylenebisphosphonate in tetrahydrofuran (235 mg) were added and the resultant mixture was stirred at 100° C. for 30 minutes. The mixture was shaken with chloroform (10 ml×2), and the organic layer was dried over magnesium sulfate and concentrated. The residue was chromatographed on a silica gel column, eluting with methanol/water to give the titled compound (145 mg).

Yield: 33%. NMR, 7.16 (d, 1H, 8.6Hz), 6.80 (dd, 1H, 2.5Hz, 8.6Hz), 6.75 (d, 1H, 2.5Hz), 5.95–5.70 (m, 2H), 5.12 (S, 2H), 4.90 (dt, 1H, 10Hz, 21.8Hz), 4.66 (t, 1H, 8.3Hz), 4.30–4.10 (m, 8H), 3.45 (s, 3H), 2.90–2.80 (m, 2H), 2.51 (t, 2H, 6.2Hz), 2.40–2.10 (m, 3H), 1.90–1.10 (m, 22H) 0.78 (s, 3H)

Preparation 36

Tetraethyl 2-carboxyethyl-1, 1-bisphosphonate

To a solution of tetramethylene diphosphonate (500 μl) in tetrahydrofuran ( 5.0 ml ) was added sodium borohydride (161 mg) under ice cooling, and the resultant mixture was stirred for 20 minutes. After confirming that generation of gas was finished, 1-bromoacetic acid benzyl ester (319 μl) was added. The reaction mixture was allowed to return to room temperature, stirred for 30 minutes, and poured into saturated aqueous ammonium chloride. The mixture was shaken with chloroform (15.0 ml×2), and the organic layer was concentrated. The residue was chromatographed on a silica gel column (20 g), eluting with chloro-form/methanol to give a colorless oil (660 mg). To a solution of this product in ethanol (10 ml) was added 10% palladium carbon (60 mg), and the mixture was hydrogenated at room temperature for 2 hours. The reaction mixture was filtered with Celite to give the titled compound (503 mg) as a colorless syrup. Yield: 72%.

NMR (CDCl$_3$, δ), 7.1–6.0 (br-S, 1H), 4.22–4.05 (m, 8H), 2.98–3.23 (m, 1H), 2.79 (dt, 2H, 6.1Hz, 16.1Hz), 1.30 (t, 12H)

Preparation 37

3-Methoxymethyloxy-17β-(3',3'-diphosphonopropiony-loxy)-1,3,5-estratriene tetraethyl To a solution of 3-methoxymethyloxy-17β-hydroxy-1,3,5-estratriene (212 mg), bisphosphonic acid ester obtained in Preparation 35, and 4-dimethylaminopyridine (107 mg) in methylene chloride (2.3 ml) was added dicyclohexyl-carbodiimide (180 mg), and the resultant mixture was stirred at room temperature for 12 hours. The reaction mixture was poured into chilled water and shaken with methylene chloride (10 ml×2), and the organic layer was concentrated to dryness. The residue was diluted with benzene (10 ml), and the solution was filtered with cotton and concentrated to give the title compound (367 mg).

Yield: 94%. NMR, 7.17 (d, 1H, 8.6Hz), 6.80 (dd, 1H, 2.6Hz, 8.6Hz), 6.74 (d, 1H, 2.6Hz), 5.12 (s, 1H, 2H), 4.67 (dd, 1H, 7.5Hz, 9.1Hz), 4.25–4.05 (m, 8H), 3.45 (s, 3H), 3.20–2.75 (m, 5H), 2.3–2.1 (m, 3H), 2.00–1.20 (m, 10H), 1.31 (t-like, 12H), 0.81 (s, 3H)

Preparation 38

17β-Hydroxy-3-(3',3'-diphosphonopropionyloxy)-1,3,5-estratriene tetraethyl

Using 17-oxo-3-(3',3'-diphosphonopropionyloxy)-1,3,5-estratriene (270 mg), the reaction was carried out in the same manner as in Preparation 36 to give 17-oxo-3-(3', 3'-diphosphono-propionyloxy)-1,3,5-estratriene (418 mg, Yield: 100%). To a solution of this product in diethyl ether (4.3 ml) was added 0.425 M solution of $Zn(BH_4)_2$ in diethyl ether (2.8 ml), and the resultant mixture was stirred at 0° C. for 30 minutes and poured into chilled water. The mixture was shaken with chloroform (15 ml×2), and the organic layer was concentrated. The residue was chromatographed on a silica gel column, eluting with chloroform/methanol to give the titled compound (275 mg).

Yield: 65%. NMR ($CDCl_3$, δ), 7.23 (d, 1H, 8.45Hz), 6.82 (dd, 1H, 2.4Hz, 8.45Hz), 6.76 (d, 1H, 2.4Hz), 4.23–4.03 (m, 8H), 3.67 (t, 1H, 8.15Hz), 3.25–2.90 (m, 3H), 2.85–2.70 (m, 2H), 2.30–1.00 (m, 13H), 1.30 (t-like, 12H), 0.72 (s, 3H)

EXAMPLE 1

[17β-(3-Hydroxy-1,3,5-estratrienyloxy)carbonylaminomethyl-carboxamidomethylene]bis(phosphonic acid) (Compound No. 1 in Table 1)

A solution of [17β-(3-methoxymethyloxy-1,3,5-estratrienyloxy)-carbonylaminomethylcarboxamidomethylene]bis(phosphonate)tetraethyl (obtained in Preparation 6) (300 mg) in acetonitrile (6 ml) was stirred at −20° C. trimethylsilyl iodide was added dropwise and stirred for 30 minutes and then mixed with water (1 ml). The resulting precipitate was filtered, washed with distilled water well, and dried to give [17β-(3-hydroxy-1,3,5-estratrienyloxy)carbonylaminomethylcarboxamidomethylene] bis(phosphonic acid) (170 mg) as colorless solid. Yield: 73%.

NMR (DMSOd-6, δ) 7.01 (1H, d, J=8.5Hz), 6.48 (1H, dd, J=2.5Hz, 8.5Hz), 6.41 (1H, d, J=2.5Hz), 4.48 (1H, t, J=4.9Hz), 3.93 (1H, dt, J=1.6Hz, 18.8Hz), 3.74 (2H, d, J=4.9Hz), 2.68 (2H, d, J=4.4Hz), 0.77 (3H, s)

EXAMPLE 2

{2-[17'β-(3'-Hydroxy-1',3',5'-estratrienyloxy)carbonylamino]-ethylcarboxamidomethylene}bis(phosphonic acid) (Compound No. 2 in Table 1)

Using {2-[17'β-(3'-methoxymethyloxy-1',3',5'-estratrieny-loxy)carbonylamino]ethylcarboxamidomethylene}bis(tetrae-thyl phoshponate) obtained in Preparation 7, the reaction was carried out in the same manner as in Example 1 to give {2-[17'β-(3'-hydroxy-1',3',5'-estratrienyloxy) carbonylamino]-ethylcarboxamidomethylene}bis(phosphonic acid). Yield: 45%.

NMR (DMSOd-6, δ) 8.09 (1H, d, J=10.0Hz), 7.02 (1H, d, J=8.5Hz), 6.90 (1H, t, J=5.0Hz), 6.48 (1H, dd, J=2.5Hz, 8.5Hz), 6.42 (1H, d, J=2.5Hz), 4.54 (1H, dt, J=10.0Hz, 21.8Hz), 4.74 (1H, t, J=8.3Hz), 3.21–3.12 (2H, m), 2.75–2.60 (2H, m), 2.38 (2H, t, J=6.9Hz), 0.74 (3H, s)

EXAMPLE 3

[17β-(3'-Hydroxy-1',3',5'-estratrienyloxy)carbonylmethyl-carboxamidomethylene]bis(phosphonic acid) (Compound No. 25 in Table 1)

To a solution of [17β-(3-methoxymethyloxy-1,3,5-estratrienyloxy)carbonylmethylcarboxamidomethylene]bis(tetraethyl-phosphonate) (350 mg) in acetonitrile (7 ml) chilled at −20° C. was added trimethylsilyl iodide (0.40 ml), and the resultant mixture was stirred at −20° C. for 30 minutes. The reaction mixture was diluted with methylene chloride (50 ml) and mixed with saturated aqueous sodium bicarbonate. The resulting precipitate was filtered, washed with ethyl acetate well, and dried to give the titled compound (145 mg) as a colorless solid. Yield: 54%.

NMR ($D_2O$, δ) 7.01 (d, 1H, J=8.3Hz), 6.48 (d, 1H, J=8.3Hz), 6.42 (s, 1H), 4.64 (t, 1H, J=8.8Hz), 3.38 (s, 2H), 2.85–2.60 (m, 2H), 2.32–1.09 (m, 13H), 0.76 (s, 3H)

EXAMPLE 4

{1-[17'β-(3'-Hydroxy-1',3',5'-estratrienyloxy)carbonyl]-1-methylethylcarboxamidomethylene}bis(phoshponic acid) and its sodium salt (Compound No. 32 in Table 1)

To a solution of {1-[17'β-(3'-methoxymethyloxy)-1',3',5'-estratrienyloxy)-carbonyl]-1-methylethylcarboxamido-methylene}bis(tetraethyl phoshponate) (230 mg) in acetonitrile (2.3 ml) chilled at −20° C. was added trimethylsilyl iodide (0.273 ml), and the resultant mixture was stirred for 30 minutes. The reaction mixture was diluted with methylene chloride (3.0 ml), and water (0.5 ml) was gradually dropwise added. The resultant precipitate was filtered, washed with ethyl acetate to give the titled compound (100 mg) as colorless solid. Yield: 56%.

To a solution of this product in methanol (3.0 ml) was dropwise added a solution of sodium acetate (43 mg) in methanol (1.0 ml), and the resultant precipitate was filtered and washed with methanol/water to give sodium salt of the titled compound (59 mg).

NMR ($D_2O$, δ), 7.04 (d, 1H, 8.2Hz), 6.48 (d, 1H, 8.2Hz), 6.45 (s, 1H), 4.07 (t, 1H, 18.6Hz), 2.70–2.50 (m, 2H), 2.10–1.0 (m, 13H), 1.34, 1.32, 0.63 (each s, each 3H)

EXAMPLE 5-12

The reaction was carried out in the same manner as in Example 4 to give sodium salts of the compounds of the following general formula.

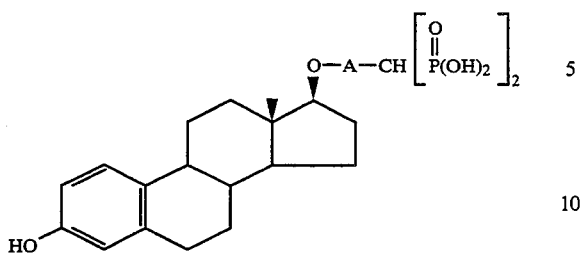

EXAMPLE 5

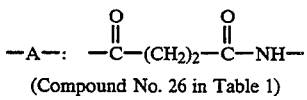

(Compound No. 26 in Table 1)

Yield: 39% NMR (D$_2$O, δ), 7.05 (d, 1H, 8.2Hz), 6.52 (d, 1H, =8.2Hz), 6.47 (s, 1H), 4.23 (t, 1H, 19.8Hz), 2.69–2.47 (m, 6H), 2.11–0.98 (m, 13H), 0.63 (s, 3H)

EXAMPLE 6

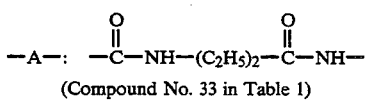

(Compound No. 33 in Table 1)

Yield: 78% NMR (D$_2$O, δ), 6.89 (d, 1H, 7.5Hz), 6.52–6.44 (m, 2H), 4.40 (t, 1H, 19.5Hz), 2.70–2.50 (m, 2H), 2.10–0.90 (m, 17H), 0.85–0.62 (m, 6H), 0.50 (s, 3H)

EXAMPLE 7

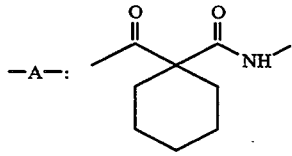

(Compound No. 35 in Table 1)

Yield: 77% NMR (D$_2$O, δ), 6.91 (d, 1H, 7.5Hz), 6.52–6.33 (m, 2H), 4.23 (t, 1H, 19.2Hz), 3.66 (t, 1H, 7.4Hz), 2.65–2.50 (m, 2H), 2.10–0.90 (m, 23H), 0.57 (s, 3H)

EXAMPLE 8

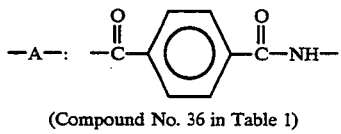

(Compound No. 36 in Table 1)

Yield: 37% NMR (D$_2$O, δ) 7.89, 7.72 (each d, each 2H, each 8.4Hz), 6.94 (d, 1H, 8.6Hz), 6.60–6..30 (m, 2H), 4.50 (t-like), 1H, with D$_2$O), 3.90–3.68 (m, 1H), 2.60–2.43 (m, 2H), 2.20–1.00 (m, 13H), 0.70 (s, 3H)

EXAMPLE 9

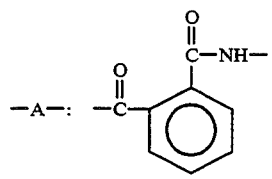

(Compound No. 38 in Table 1)

Yield: 93% NMR (D$_2$O, δ), 7.80–7.50 (m, 3H), 7.50–7.30 (m, H), 7.09 (d, 1H, 8.2Hz), 7.60–7.40 (m, 2H), 4.73 (t, 1H, 7.4Hz), 4.53 (t, 1H, 19.8Hz), 2.70–2.50 (m, 2H), 2.30–1.10 (m, 13H), 0.71 (s, 3H)

EXAMPLE 10

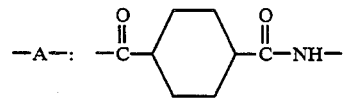

(Compound No. 39 in Table 1)

Yield: 90% NMR (D$_2$O, δ), 7.06 (d, 1H, 7.6Hz), 6.70–6.50 (m, 2H), 4.35 (d, 1H, 18.6Hz), 2.8–2.6 (m, 2H), 2.40–1.00 (m, 17H), 0.67 (s, 3H)

EXAMPLE 11

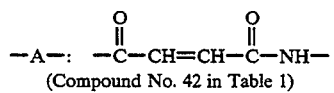

(Compound No. 42 in Table 1)

Yield: 46% NMR (D$_2$O, δ), 7.2–7.1 (m, 2H), 6.7–6.4 (m, 3H), 4.4–4.0 (m, 1H), 2.7–2.5 (m, 2H), 2.2–1.0 (m, 13H), 0.66 (s, 3H)

EXAMPLE 12

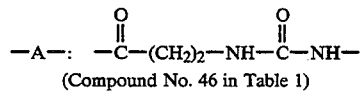

(Compound No. 46 in Table 1)

Yield: 82% NMR (D$_2$O, δ), 7.18 (d, 1H, 7.6Hz), 6.7–6.4 (m, 2H), 4.23 (t, 1H, 18.6Hz), 3.52 (t, 1H, 7.8Hz), 2.80–2.60 (m, 6H), 2.2–0.9 (m, 13H), 0.53 (s, 3H)

EXAMPLES 13–15

In the same manner as in Examples 5–12, the compounds of the following general formula were obtained.

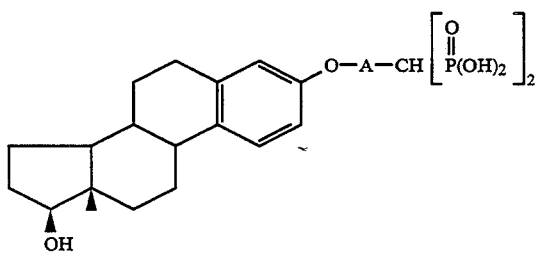

EXAMPLE 13

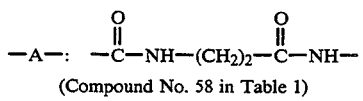
(Compound No. 58 in Table 1)

Yield: 84% NMR (D$_2$O, δ), 7.24 (d, 1H, 8.2Hz), 6.90–6.70 (m, 2H), 4.33 (t, 1H, 18.6Hz), 3.60 (t, 1H, 7.4Hz), 3.43–3.30 (m, 2H), 2.80–2.70 (m, 2H), 2.60–2.40 (m, 2H), 2.30–1.10 (m, 13H), 0.62 (s, 3H)

EXAMPLE 14

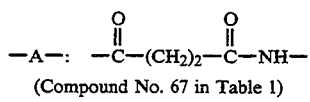
(Compound No. 67 in Table 1)

Yield: 87% NMR (D$_2$O, δ), 7.18 (d, 1H, 8.4Hz), 6.70–6.60 (m, 2H), 4.23 (t, 1H, 18.6Hz), 3.51 (t, 1H, 7.5Hz), 2.80–2.55 (m, 6H), 2.20–0.95 (m, 13H), 0.53 (s, 3H)

EXAMPLE 15

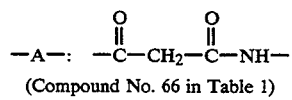
(Compound No. 66 in Table 1)

Yield: 88% NMR (D$_2$O, δ), 7.26 (d, 1H, 8.3Hz), 6.85–6.75 (m, 2H), 4.33 (t, 1H, 18.6Hz), 3.58 (t, 1H, 7.8Hz), 3.18 (s, H), 2.80–2.70 (m, 2H), 2.30–1.00 (m, 15H), 0.59 (s, 3H)

EXAMPLES 16–19

In the same manner as in Examples 5–12, the compounds of the following general formula were obtained.

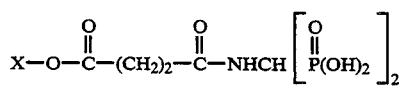

EXAMPLE 16

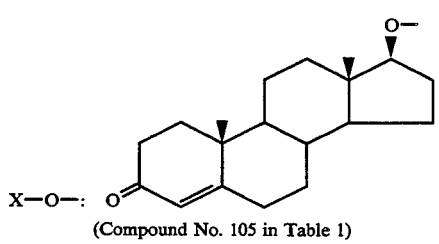
(Compound No. 105 in Table 1)

Yield: 90% NMR (D$_2$O, δ), 5.75 (s-like, 1H), 4.48 (t, 1H, 7.6Hz), 4.20 (t, 1H, 20Hz), 2.6–0.6 (m, 18H), 0.75 (s-like, 6H)

EXAMPLE 17

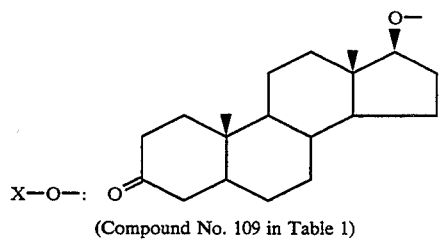
(Compound No. 109 in Table 1)

Yield: 95% NMR (D$_2$O, δ), 4.46 (t, 1H, 7.6Hz), 4.22 (t, 1H, 10Hz), 2.6–0.6 (m, 22H), 0.65 (s, 6H)

EXAMPLE 18

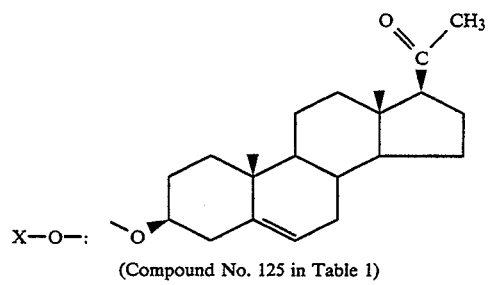
(Compound No. 125 in Table 1)

Yield: 93% NMR (D$_2$O, δ), 5.32 (s-like, 1H), 4.5–4.3 (m, 1H), 4.25 (t, 1H, 22.5Hz), 2.6–0.9 (m, 24H), 2.21, 0.89, 0.45 (each s, 3H)

EXAMPLE 19

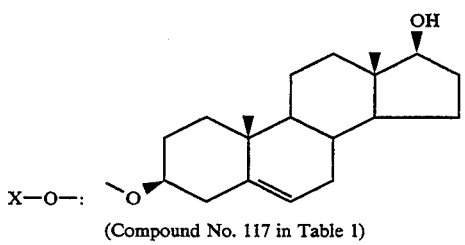
(Compound No. 117 in Table 1)

Yield: 72% NMR (D$_2$O, δ), 5.4–5.2 (m, 1H), 4.5–4.3 (m, 1H), 4.21 (t, 1H, 18.6Hz), 3.45 (t, 1H, 7.7Hz), 2.6–0.95 (m, 23H), 0.86, 0.55 (each s, 3H)

EXAMPLES 20, 21

In the same manner as in Examples 5–12, the compounds of the following general formula were obtained.

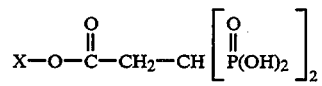

EXAMPLE 20

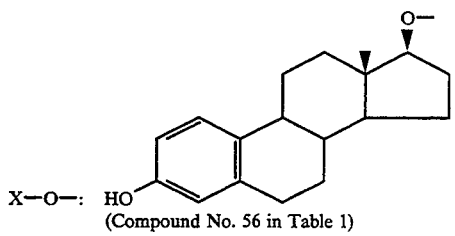

X—O—: (Compound No. 56 in Table 1)

Yield: 91% NMR (D₂O, δ), 7.05 (d, 1H, 8.7Hz), 6.50 (d, 1H, 8.7Hz), 6.47 (s, 1H), 2.70–2.30 (m, 5H), 2.20–1.00 (m, 13H), 0.59 (s,3H).

EXAMPLE 21

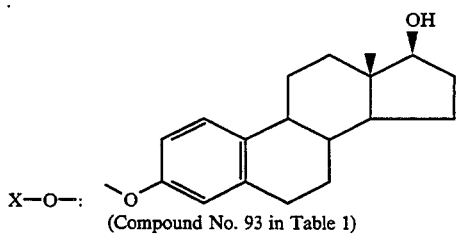

X—O—: (Compound No. 93 in Table 1)

Yield: 65% NMR (D₂O, δ), 7.21 (d, 1H, 8.7Hz), 6.80–6.70 (m, H), 3.53 (t, 1H, 7.4Hz), 2.9–1.0 (m, 18H), 0.72 (s, 3H)

EXAMPLES 22, 23

In the same manner as in Examples 5–12, the compounds of the following general formula were obtained.

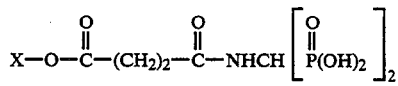

EXAMPLE 22

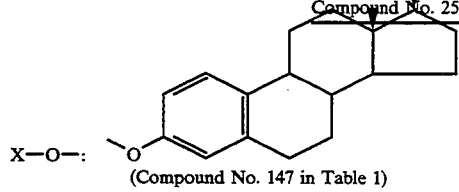

X—O—: (Compound No. 147 in Table 1)

Yield: 93% NMR (D₂O, δ), 7.20–7.00 (m, 1H), 6.80–6.60 (m, 2H), 4.60–4.40 (m, 1H), 4.33 (t, 1H, 18.1Hz), 2.90–0.95 (m, 19H), 2.00, 0.60 (each s, 3H)

EXAMPLE 23

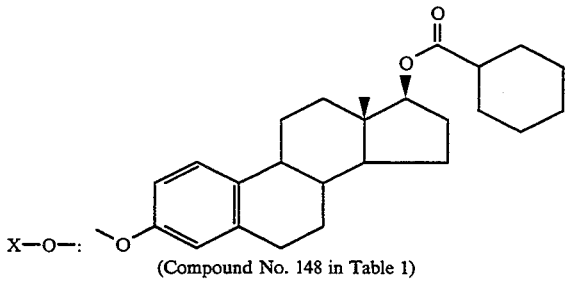

X—O—: (Compound No. 148 in Table 1)

Yield: 83% NMR (D₂O, δ), 7.20–7.00 (m, 1H), 6.80, 6.60 (m, 2H), 4.60–4.40 (m, 1H), 4.33 (t, 1H, 18Hz), 2.90–0.95 (m, 30H), 0.60 (s, 3H)

Experiment 1 Transitional ability of the compound of the invention to bones

Test Method

SD male rat (body weight about 220 g) subcutaneously received a vehicle (95% corn oil and 5% benzyl alcohol) (Group A) or 17β-estradiol (250 μg/kg) (Group B) or equimolar amount of the compound of the present invention [17β-(3-hydroxy-1,3,5-estratrienenyloxy)carbonylmethylcarboxamidomethylene]-bis(phosphonic acid) (Compound No. 25 in Table 1: hereinafter referred to as "Compound No. 25") (500 μg/kg) (Group C). The blood and the tibia were collected after 2 hours, one day, and two days in each group. 17β-Estradiol in the plasma was measured directly by RIA method. The tibia was pulverized after removing the meat chip and marrow, and then lyophilized. The pulverized bone (150 mg) was dissolved in 5 N hydrochloric acid (1.5 ml) at room temperature, and the resultant solution (500 μl) was mixed with 0.5 M EDTA (500 μl), water (1 ml) and 5 N sodium hydroxide (500 μl), and allowed to stand at room temperature for 30 minutes to isolate 17β-estradiol of Compound No. 25. The isolated 17β-estradiol was extracted with 5 ml of isoamyl alcohol, and the extract was concentrated to dryness and dissolved in 500 μl of phosphate buffer (pH 7.4) for assaying by RIA method.

Test Result

Table 2 shows a mean value of the measurements for one group consisting of five rats with standard error.

TABLE 2

| | Amount of 17β-estradiol in Plasma and in Bone | | | | | |
|---|---|---|---|---|---|---|
| | 2 Hour | | 1 Day | | 2 Days | |
| Compound administered | Plasma (pg/ml) | Bone (pg/100 mg) | Plasma (pg/ml) | Bone (pg/100 mg) | Plasma (pg/ml) | Bone (pg/100 mg) |
| Vehicle | <20 | <20 | <20 | <20 | <20 | <20 |
| 17β-Estradiol | 5187 ± 846 | <20 | 102 ± 30 | <20 | <20 | <20 |
| Compound No. 25 | <20 | 51 ± 25 | <20 | 359 ± 134 | <20 | 376 ± 92 |

The table shows that, in Group B, 17β-estradiol was detected in plasma until the next day after administration but it was below detection limit in bone throughout the test period. On the other hand, in Group C in which Compound No. 25 was administered, 17β-estradiol was below detection limit in plasma, and it was detected in bone already 2 hours after administration. The amount of 17β-estradiol in bone increased with the lapse of time. Accordingly, it was concluded that Compound No. 25 of the present invention has an ability of transition into bone.

Experiment 2 Bone resorption inhibitory action observed in ovariectomy model

Test Method

SD female rats of 12 weeks age which had undergone ovareectomy (OVX) received subcutaneously a vehicle (95% corn oil and 5% benzyl alcohol) (Group 2) or 17β-estradiol (20 μg/kg) (Group 3) or equimolar amount of Compound No. 25 (40 μg/kg) (Group 4) for 28 days since the next day of operation. The rats were subjected to autopsy on 29th day, and the weight of wet uterus and the amount of a bone volume in tibia (Cancellous bone volume/Tissue volume×100) were measured.

Test Result

Table 3 shows a mean value of the measurements for one group consisting of 10 rats with standard error.

TABLE 3

| Bone resorption inhibitory effect of compound No. 25 | | |
|---|---|---|
| Group | | Bone volume (BV/TV, %) |
| 1 | Sham operation: Administration of vehicle | 26 ± 2 |
| 2 | OVX: Administration of vehicle | 18 ± 2 |
| 3 | OVX: Administration of 17β-Estradiol | 30 ± 2 |
| 4 | OVX: Administration of Compound No. 25 | 30 ± 3 |

Group 1 vs, Group 2; P < 0.01
Group 2 vs, Group 3; P < 0.001
Group 2 vs, Group 4; P < 0.01
(Statistics was conducted according to Student t-test.)

Bone volume was significantly lowered in OVX group than in the sham operation group (Group 1). In Group 3 and Group 4, the bone resorption was significantly inhibited. On the other hand, the weight of uterus increased in Group 3 up to the level of Group 1, but no effect was observed in Group 4 in this respect. As the result of the above test, it was concluded that Compound No. 25 acts osteoselectively and shows significant bone resorption inhibitory action without giving the uterus weight gain.

The compounds of the present invention allow a steroid compound to act more selectively to bone tissue than to other organs and are useful as therapeutic agents to bone metabolism diseases like osteoporosis, without giving actions to other organs due to their high selectivity to bone tissue.

What is claimed is:

1. A steroid derivative of the following general formula (I):

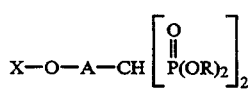
(I)

wherein X—O— represents the residue of a steroid compound which is represented by the following formula:

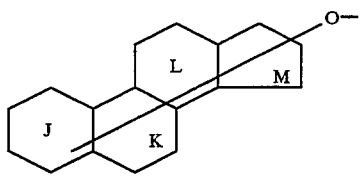

wherein the rings J, K, L and M each independently represent a saturated, partially saturated, or unsaturated ring, and which may be independently substituted by one or more substituents selected from alkyl, alkenyl, alkynyl, halogen, alkoxy ester, acyl, hydroxy and oxo groups, —A— represents

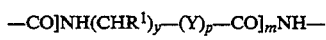

in which y represents an integer of from 1 to 3, p represents 0 or 1, m represents an integer of from 0 to 5, $R^1$ represents hydrogen atom, optionally substituted $C_1$-$C_4$ alkyl group or optionally substituted $C_6$-$C_{14}$ aryl group, and Y represents —O— or —NH—,

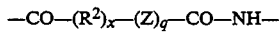

in which x and q each independently represent 0 or 1, $R^2$ represents optionally substituted vinylene group,

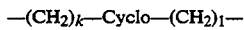

in which k and l each represent an integer of 0–5, and Cycle represents $C_3$-$C_7$ cycloalkylene group, optionally substituted phenylene group or optionally substituted $C_1$-$C_7$ alkylene group, and Z represents —O— or —NH—, or

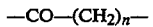

in which n represents an integer of from 0 to 10 with proviso that, when X—O— is 17β-(3-hydroxy-1,3,5-estratrieneyloxy) group, n represents 0 or 1, and R represents hydrogen atom or $C_1$-$C_4$ alkyl group, or a pharmaceutically acceptable salt thereof.

2. A compound according to claim 1, wherein said steroid compound is estradiol, testosterone, dehydrotestosterone, pregnenolone, ethynylestradiol, estrone, estriol, dehydroepiandrosterone, androstenediol, 17α-hydroxyprogesterone, norethanedodrone, androsterone, norethidrone or nandrodone.

3. A compound according to claim 1, wherein said steroid compound is estradiol, testosterone, dehydrotestosterone, pregnenolone or ethynylestradiol.

4. A compound according to claim 3, wherein —A— is

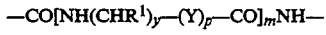

which y represents an integer of from 1 to 3, p represents 0, m represents 1, and $R^1$ represents hydrogen atom or optionally substituted $C_1$-$C_4$ alkyl group,

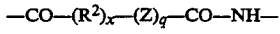

in which x represents 1, q represents 0 or 1, $R^2$ represents vinylene group,

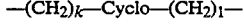

in which k and l each represent an integer of 0–5, and Cyclo represents $C_3$–$C_7$ cycloalkylene group, phenylene group or optionally substituted $C_1$–$C_5$ alkylene group, and Z represents —NH—, or —CO—$(CH_2)_n$— in which n represents an integer of from 0 to 10.

5. A compound according to claim 4, wherein $R^1$ is hydrogen atom or $C_1$–$C_4$ alkyl group optionally substituted by phenyl group.

6. A compound according to claim 4, wherein $R^2$ is vinylene group,

—$(CH_2)_k$—Cyclo—$(CH_2)_l$— in which k and l each represent an integer of 0–5, and Cyclo represents $C_3$–$C_7$ cycloalkylene group, phenylene group or $C_1$–$C_5$ alkylene group optionally substituted by one or two $C_1$–$C_5$ alkyl groups.

7. A pharmaceutical composition comprising a steroid derivative described in claim 1 or a pharmaceutically acceptable salt thereof together with a pharmaceutically acceptable carrier.

8. A therapeutic agent for use in osteopathy comprising a steroid derivative described in claim 1 or a pharmaceutically acceptable salt as an effective ingredient.

9. A compound according to claim 4, wherein X—O— represents 3-(17$\beta$-hydroxy-1,3,5-estratrienyloxy), —A— represents —CO—[NH(CHR')$_y$—(Y)$_p$—CO]$_m$NH— in which y represents 2, p represents 0, m represents 1, and R' represents hydrogen atom and R represents hydrogen.

10. A compound according to claim 4, wherein X—O— represents 17-$\beta$(3-hydroxy-1,3,5-estratrienyloxy), —A— represents —CO—($R^2$)$_x$—(Z)$_q$—CO—NH— in which X represents 1, q represents 0, $R^2$ represents methylene or phenylene, and R represents hydrogen atom.

* * * * *